United States Patent
Cao et al.

(10) Patent No.: US 10,677,942 B2
(45) Date of Patent: Jun. 9, 2020

(54) X-RAY DETECTORS CAPABLE OF MANAGING CHARGE SHARING

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 16/068,152

(22) PCT Filed: Feb. 1, 2016

(86) PCT No.: PCT/CN2016/073034
§ 371 (c)(1),
(2) Date: Jul. 5, 2018

(87) PCT Pub. No.: WO2017/132789
PCT Pub. Date: Aug. 10, 2017

(65) Prior Publication Data
US 2019/0018153 A1 Jan. 17, 2019

(51) Int. Cl.
*G01T 1/29* (2006.01)
*G01T 1/24* (2006.01)
(Continued)

(52) U.S. Cl.
CPC .............. *G01T 1/2928* (2013.01); *A61B 6/42* (2013.01); *G01N 23/04* (2013.01); *G01T 1/24* (2013.01); *G01T 1/247* (2013.01)

(58) Field of Classification Search
CPC .......... G01T 1/2928; G01T 1/24; G01N 23/04; A61B 6/42
(Continued)

(56) References Cited

U.S. PATENT DOCUMENTS 5,825,033 A * 10/1998 Barrett .............. H01L 27/14658
250/370.1
7,479,639 B1 * 1/2009 Shahar ...................... G01T 1/17
250/370.06
(Continued)

FOREIGN PATENT DOCUMENTS

CN 201622252 U 11/2010
CN 103022066 A 4/2013
(Continued)

OTHER PUBLICATIONS

X. Llopart et al. "Medipix2: a 64-k Pixel Readout Chip With 55-μm Square Elements Working in Single Photon Counting Mode.", IEEE Transactions on Nuclear Science, vol. 49, No. 5, Oct. 31, 2002 (Oct. 31, 2002), ISSN: 0018-9499, pp. 2280, 2282-2283.

*Primary Examiner* — Taeho Jo
(74) *Attorney, Agent, or Firm* — IPro, PLLC; Qian Gu

(57) ABSTRACT

An apparatus suitable for detecting X-ray is disclosed. In one example, the apparatus comprises an X-ray absorption layer comprising a first pixel and a second pixel, and a controller. The controller is configured for determining that carriers generated by a single X-ray photon are collected by the first pixel and the second pixel. The controller is also configured for determining energy of the single X-ray photon based on a first voltage detected from the first pixel and a second voltage detected from the second pixel. The first voltage and the second voltage are caused by the single X-ray photon.

28 Claims, 29 Drawing Sheets

(51) Int. Cl.
*A61B 6/00* (2006.01)
*G01N 23/04* (2018.01)

(58) Field of Classification Search
USPC .................................................. 250/370.09
See application file for complete search history.

(56) References Cited

U.S. PATENT DOCUMENTS

| | | | |
|---|---|---|---|
| 7,488,945 B2 | 2/2009 | Li et al. | |
| 2004/0046101 A1* | 3/2004 | Nakamura | H01L 27/14643 250/200 |
| 2006/0056581 A1 | 3/2006 | Hoffman et al. | |
| 2007/0023853 A1 | 2/2007 | Partain et al. | |
| 2009/0109313 A1* | 4/2009 | Liu | H04N 5/343 348/308 |
| 2010/0213353 A1* | 8/2010 | Dierickx | G01T 1/17 250/214 R |
| 2011/0017918 A1* | 1/2011 | Baeumer | G01T 1/2018 250/370.11 |
| 2011/0210235 A1* | 9/2011 | Dierickx | G01T 1/17 250/214 R |
| 2012/0161016 A1* | 6/2012 | Schmitt | G01T 1/17 250/370.06 |
| 2012/0305786 A1* | 12/2012 | Dierickx | G01J 1/44 250/371 |
| 2013/0043399 A1* | 2/2013 | Rohr | G01T 1/243 250/366 |
| 2013/0136233 A1* | 5/2013 | Okada | G01T 1/247 378/62 |
| 2013/0206994 A1* | 8/2013 | Kaufmann | G01T 1/2006 250/366 |
| 2013/0256542 A1* | 10/2013 | Soh | G01T 1/247 250/370.09 |
| 2013/0284940 A1* | 10/2013 | Herrmann | G01T 1/17 250/393 |
| 2014/0158900 A1* | 6/2014 | Yoon | G01T 1/247 250/394 |
| 2014/0175299 A1* | 6/2014 | Spahn | G01T 1/2928 250/394 |
| 2014/0353514 A1 | 12/2014 | Unfors | |
| 2015/0244962 A1* | 8/2015 | Sonoda | H04N 5/3745 250/208.1 |
| 2015/0369929 A1* | 12/2015 | Durst | G01T 1/2018 250/362 |
| 2016/0084964 A1* | 3/2016 | Kimura | A61B 6/4241 378/4 |
| 2016/0238717 A1* | 8/2016 | Abraham | G01T 1/17 |
| 2016/0266054 A1* | 9/2016 | Cao | A61B 6/4241 |
| 2016/0285419 A1* | 9/2016 | Milkov | H04N 5/3745 |

FOREIGN PATENT DOCUMENTS

| | | |
|---|---|---|
| CN | 103995013 A | 8/2014 |
| JP | 2015135300 A | 7/2015 |
| TW | 201447956 A | 12/2014 |
| WO | 2007058600 A1 | 5/2007 |

* cited by examiner

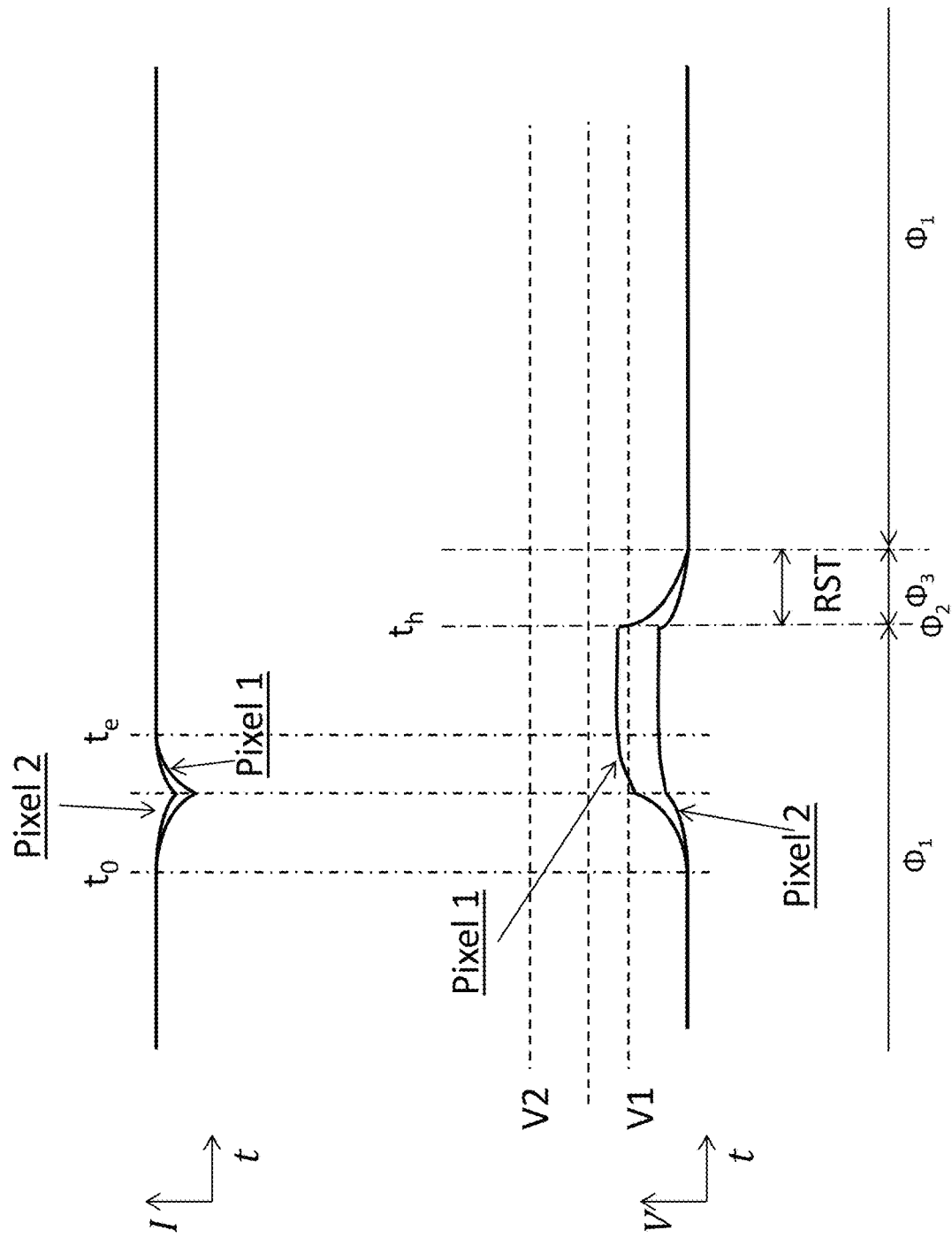

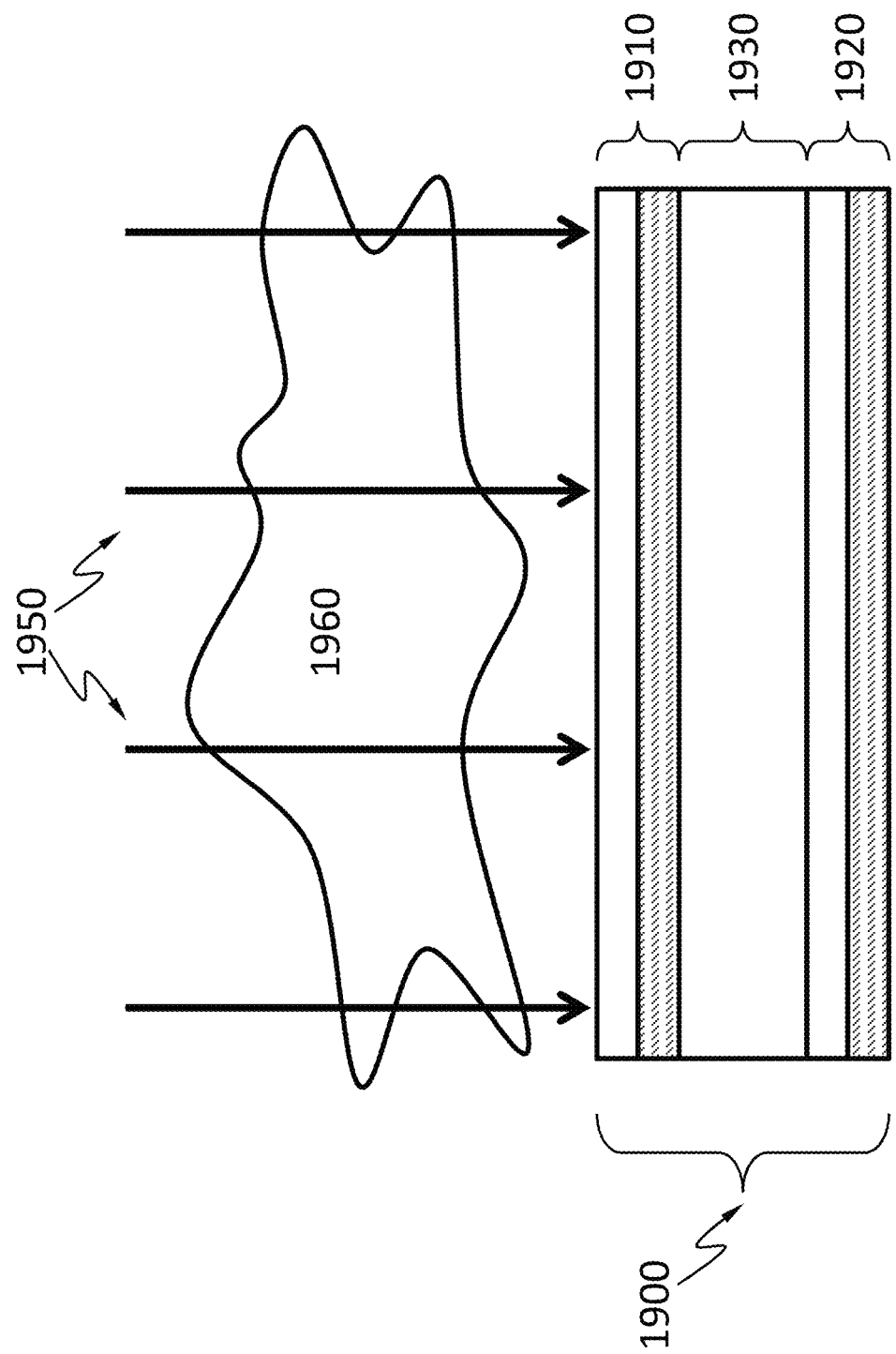

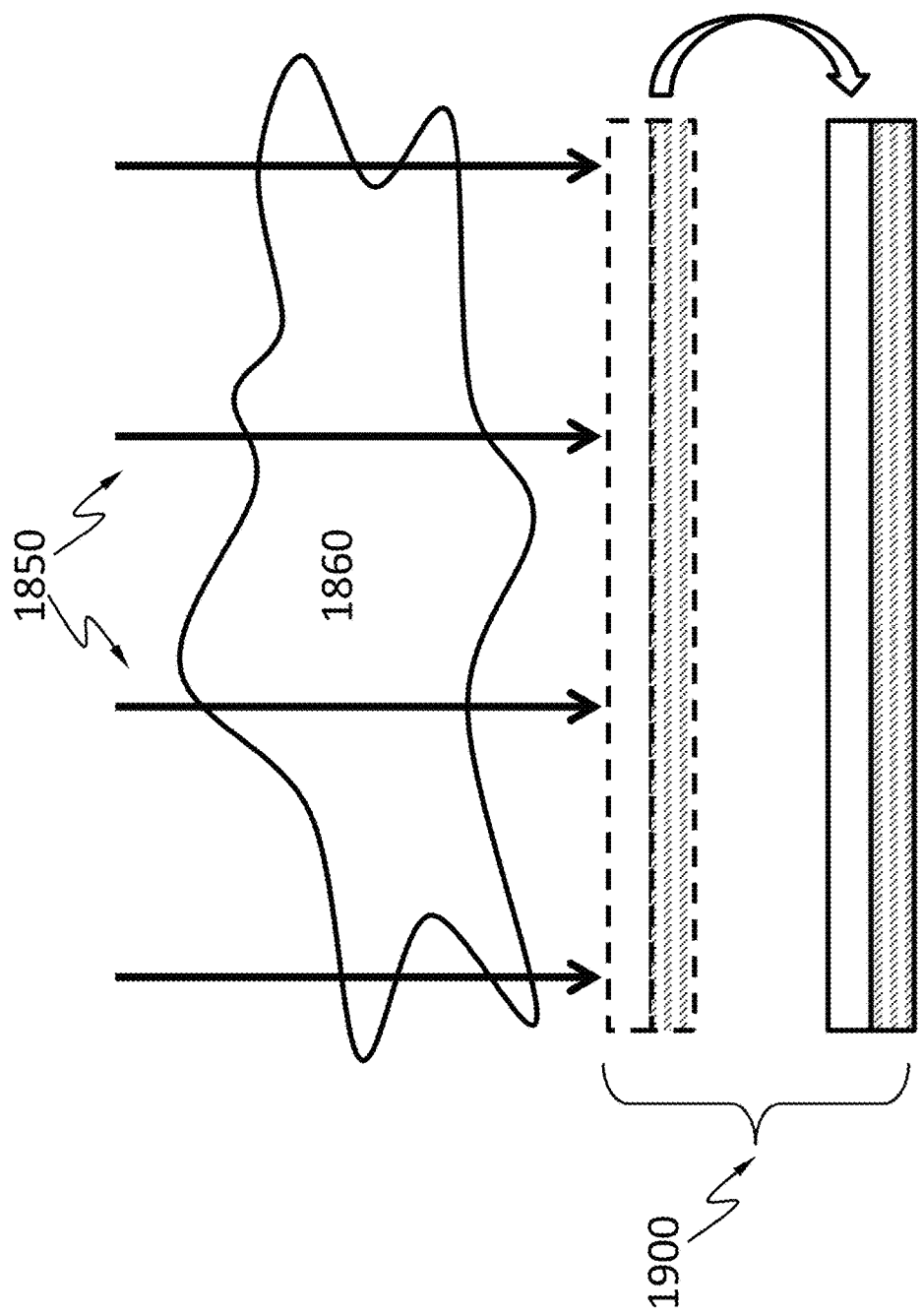

X-RAY DETECTORS CAPABLE OF MANAGING CHARGE SHARING

TECHNICAL FIELD

The disclosure herein relates to X-ray detectors, particularly relates to X-ray detectors capable of managing charge sharing.

BACKGROUND

X-ray detectors may be devices used to measure the flux, spatial distribution, spectrum or other properties of X-rays.

X-ray detectors may be used for many applications. One important application is imaging. X-ray imaging is a radiography technique and can be used to reveal the internal structure of a non-uniformly composed and opaque object such as the human body. Another important application is elemental analysis. Elemental analysis is a process where a sample of some material is analyzed for its elemental composition.

Early X-ray detectors include photographic plates and photographic films. A photographic plate may be a glass plate with a coating of light-sensitive emulsion.

In the 1980s, photostimulable phosphor plates (PSP plates) became available. A PSP plate may contain a phosphor material with color centers in its lattice. When the PSP plate is exposed to X-ray, electrons excited by X-ray are trapped in the color centers until they are stimulated by a laser beam scanning over the plate surface. As the plate is scanned by laser, trapped excited electrons give off light, which is collected by a photomultiplier tube. The collected light is converted into a digital image.

Another kind of X-ray detectors are X-ray image intensifiers. In an X-ray image intensifier, X-ray first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident X-ray. The emitted electrons are projected, through electron optics, onto an output phosphor and cause the output phosphor to produce a visible-light image.

Scintillators operate somewhat similarly to X-ray image intensifiers in that scintillators (e.g., sodium iodide) absorb X-ray and emit visible light, which can then be detected by a suitable image sensor for visible light.

Semiconductor X-ray detectors can directly convert X-ray into electric signals and thus offer better performance than previous generations of X-ray detectors. A semiconductor X-ray detector may include a semiconductor layer that absorbs X-ray in wavelengths of interest. When an X-ray photon is absorbed in the semiconductor layer, multiple charge carriers (e.g., electrons and holes) are generated. As used herein, the term "charge carriers," "charges" and "carriers" are used interchangeably. A semiconductor X-ray detector may have multiple pixels that can independently determine the local intensity of X-ray and X-ray photon energy. The charge carriers generated by an X-ray photon may be swept under an electric field into the pixels. If the charge carriers generated by a single X-ray photon are collected by more than one pixel ("charge sharing"), the performance of the semiconductor X-ray detector may be negatively impacted. In applications (e.g., elemental analysis) where X-ray photon energy is determined, charge sharing is especially problematic for accurate photon energy measurement, because the energy of an X-ray photon is determined by the amount of electric charges it generates.

SUMMARY

The teachings disclosed herein relate to methods, systems, and apparatus for X-ray detection. More particularly, the present teaching relates to methods, systems, and apparatus for X-ray detection with charge sharing management.

In one example, an apparatus suitable for detecting X-ray is disclosed. The apparatus comprises an X-ray absorption layer comprising a first pixel and a second pixel, and a controller. The controller is configured for determining that carriers generated by a single X-ray photon are collected by the first pixel and the second pixel. The controller is also configured for determining energy of the single X-ray photon based on a first voltage detected from the first pixel and a second voltage detected from the second pixel, wherein the first voltage and the second voltage are caused by the single X-ray photon.

According to an embodiment, the controller is further configured for obtaining a sum of an absolute value of the first voltage and an absolute value of the second voltage. The controller is further configured for determining the energy of the single X-ray photon based on the sum.

According to an embodiment, the first pixel is associated with a first capacitor charged with the first voltage; the second pixel is associated with a second capacitor charged with the second voltage; and the sum is obtained by serially connecting the first capacitor and the second capacitor and measuring a voltage across the serially connected capacitors.

According to an embodiment, the sum is obtained by numerically adding the absolute value of the first voltage and the absolute value of the second voltage.

According to an embodiment, the apparatus comprises a counter configured for registering a number of X-ray photons absorbed by the X-ray absorption layer, wherein the controller is configured for causing the number registered by the counter to increase by one, if the sum equals or exceeds a predetermined threshold.

According to an embodiment, the energy of the single X-ray photon is determined when a rate of change of the first voltage and a rate of change of the second voltage are substantially zero.

According to an embodiment, the controller is configured for determining that carriers generated by a single X-ray photon are collected by the first pixel and the second pixel, if the first voltage and the second voltage start to change in a same time period.

According to an embodiment, the controller is configured for determining that carriers generated by a single X-ray photon are collected by the first pixel and the second pixel, if an absolute value of the first voltage and an absolute value of the second voltage reach a first threshold in a same time period.

According to an embodiment, the X-ray photon is assigned to one of the first pixel and the second pixel to form an image, based on at least one of the following: a comparison of the first voltage and the second voltage; and relative positions of the two pixels.

According to an embodiment, the apparatus comprises an array of pixels.

Disclosed herein is a system comprising the apparatus described above and an X-ray source. The system is configured for performing X-ray radiography on human chest or abdomen.

Disclosed herein is a system comprising the apparatus described above and an X-ray source. The system is configured for performing X-ray radiography on human mouth.

Disclosed herein is a cargo scanning or non-intrusive inspection (NII) system, comprising the apparatus described above and an X-ray source. The cargo scanning or non-intrusive inspection (NII) system is configured for forming an image based on backscattered X-ray.

Disclosed herein is a cargo scanning or non-intrusive inspection (NII) system, comprising the apparatus described above and an X-ray source. The cargo scanning or non-intrusive inspection (NII) system is configured to form an image using X-ray transmitted through an object inspected.

Disclosed herein is a full-body scanner system comprising the apparatus described above and an X-ray source.

Disclosed herein is an X-ray computed tomography (X-ray CT) system comprising the apparatus described above and an X-ray source.

Disclosed herein is an electron microscope comprising the apparatus described above, an electron source and an electronic optical system.

Disclosed herein is a system comprising the apparatus described above. The system is configured for measuring dose of an X-ray source.

Disclosed herein is a system comprising the apparatus described above. The system is an X-ray telescope, or an X-ray microscopy, or a system configured to perform mammography, industrial defect detection, microradiography, casting inspection, weld inspection, or digital subtraction angiography.

In another example, a method is disclosed. The method comprises: determining that carriers generated by a single X-ray photon are collected by a first pixel and a second pixel; detecting a first voltage from the first pixel; detecting a second voltage from the second pixel; and determining energy of the single X-ray photon based on the first voltage and the second voltage, wherein the first voltage and the second voltage are caused by the single X-ray photon.

According to an embodiment, the method further comprises: obtaining a sum of an absolute value of the first voltage and an absolute value of the second voltage, wherein the first voltage and the second voltage are caused by the single X-ray photon; and determining the energy of the single X-ray photon based on the sum.

According to an embodiment, the first pixel is associated with a first capacitor charged with the first voltage; the second pixel is associated with a second capacitor charged with the second voltage; and the sum is obtained by serially connecting the first capacitor and the second capacitor and measuring a voltage across the serially connected capacitors.

According to an embodiment, the sum is obtained by numerically adding the absolute value of the first voltage and the absolute value of the second voltage.

According to an embodiment, the method further comprises increasing a count of X-ray photon incident on an X-ray absorption layer comprising the first pixel and the second pixel by one, if the sum equals or exceeds a predetermined threshold.

According to an embodiment, the energy of the single X-ray photon is determined when a rate of change of the first voltage and a rate of change of the second voltage are substantially zero.

According to an embodiment, carriers generated by the single X-ray photon are determined to be collected by the first pixel and the second pixel, if the first voltage and the second voltage start to change in a same time period.

According to an embodiment, carriers generated by the single X-ray photon are determined to be collected by the first pixel and the second pixel, if an absolute value of the first voltage and an absolute value of the second voltage reach a first threshold in a same time period.

According to an embodiment, the X-ray photon is assigned to one of the first pixel and the second pixel to form an image, based on at least one of the following: a comparison of the first voltage and the second voltage; and relative positions of the two pixels.

Disclosed herein is a system suitable for phase-contrast X-ray imaging (PCI), the system comprising: the apparatus described above, a second X-ray detector, and a spacer. The apparatus and the second X-ray detector are spaced apart by the spacer.

According to an embodiment, the apparatus and the second X-ray detector are configured to respectively capture an image of an object simultaneously.

According to an embodiment, the second X-ray detector is identical to the apparatus.

Disclosed herein is a system suitable for phase-contrast X-ray imaging (PCI), the system comprising the apparatus described above. The apparatus is configured to move to and capture images of an object exposed to incident X-ray at different distances from the object.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

FIG. 7 schematically shows temporal changes of the electric currents flowing through the two neighboring electrodes (upper curves) where at least one current is caused by noise (e.g., dark current), and corresponding temporal changes of the voltages of the electrodes (lower curves), in the electronic system operating in the way shown in FIG. 6, according to an embodiment;

FIG. 10 schematically shows a system suitable for phase-contrast X-ray imaging (PCI), according to an embodiment;

FIG. 11 schematically shows a system suitable for phase-contrast X-ray imaging (PCI), according to an embodiment;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

When an X-ray photon is absorbed in a semiconductor layer of an X-ray detector having an array of pixels, multiple charge carriers (e.g., electrons and holes) are generated and may be swept under an electric field towards circuitry for measuring these charge carriers. The carriers drift along the direction of the electric field and diffuse in all directions. The envelope of carrier trajectories can be roughly a conical shape. If the envelope sits on a boundary of two or more pixels of the X-ray detector, charge sharing occurs ("charge sharing" used in the present teachings means charge carriers generated from a single X-ray photon are collected by two or more pixels). Charge sharing may cause inaccurate measurement of an X-ray photon energy, because the energy of the X-ray photon is determined by the amount of electric charges it generates.

In the present teaching, when it is determined that neighboring pixels share charges generated by a single photon, voltages detected at the pixels are added, e.g. after stabilization of the voltages on these pixels. In one example, the voltages may be added by using physical capacitors that can be connected in serial. In another example, each of the neighboring pixels reads its own voltage and the voltages are numerically added. The added sum of the voltages can then be utilized to accurately measure the energy of the photon that is shared by the neighboring pixels.

When the X-ray detector is configured for sensing an image, the photon may be assigned to one of the neighboring pixels to form an image, based on relative positions of the neighboring pixels and/or a comparison of the voltages of the neighboring pixels.

Figure 1A:
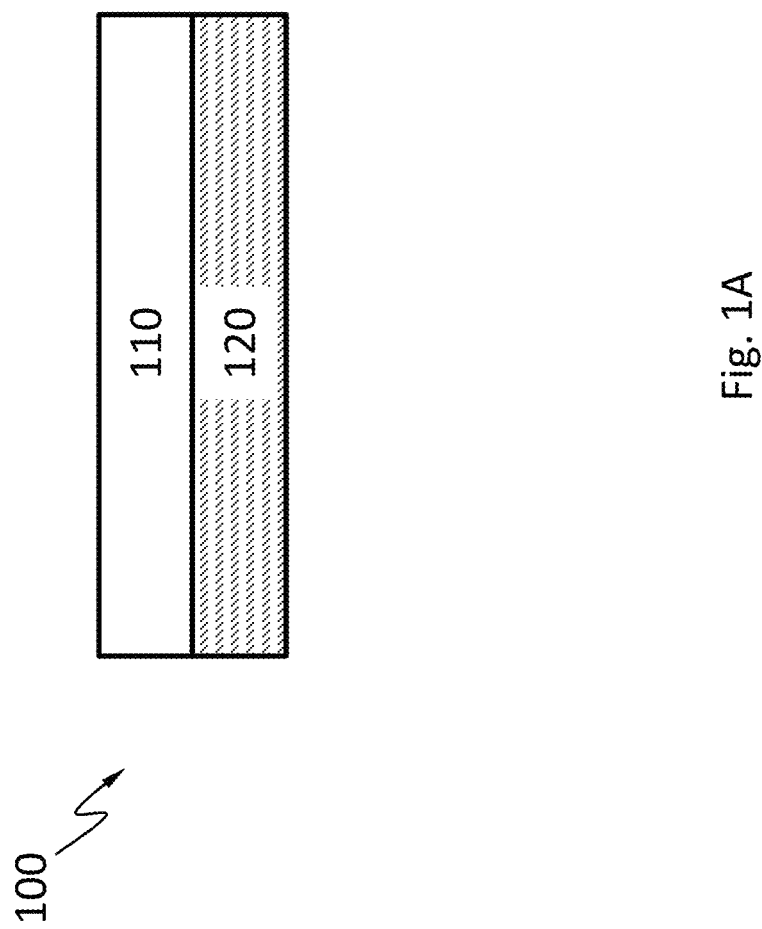
FIG. 1A schematically shows a cross-sectional view of the detector, according to an embodiment.

FIG. 1A schematically shows a semiconductor X-ray detector 100, according to an embodiment. The semiconductor X-ray detector 100 may include an X-ray absorption layer 110 and an electronics layer 120 (e.g., an ASIC) for processing or analyzing electrical signals incident X-ray generates in the X-ray absorption layer 110. In an embodiment, the semiconductor X-ray detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 1B:
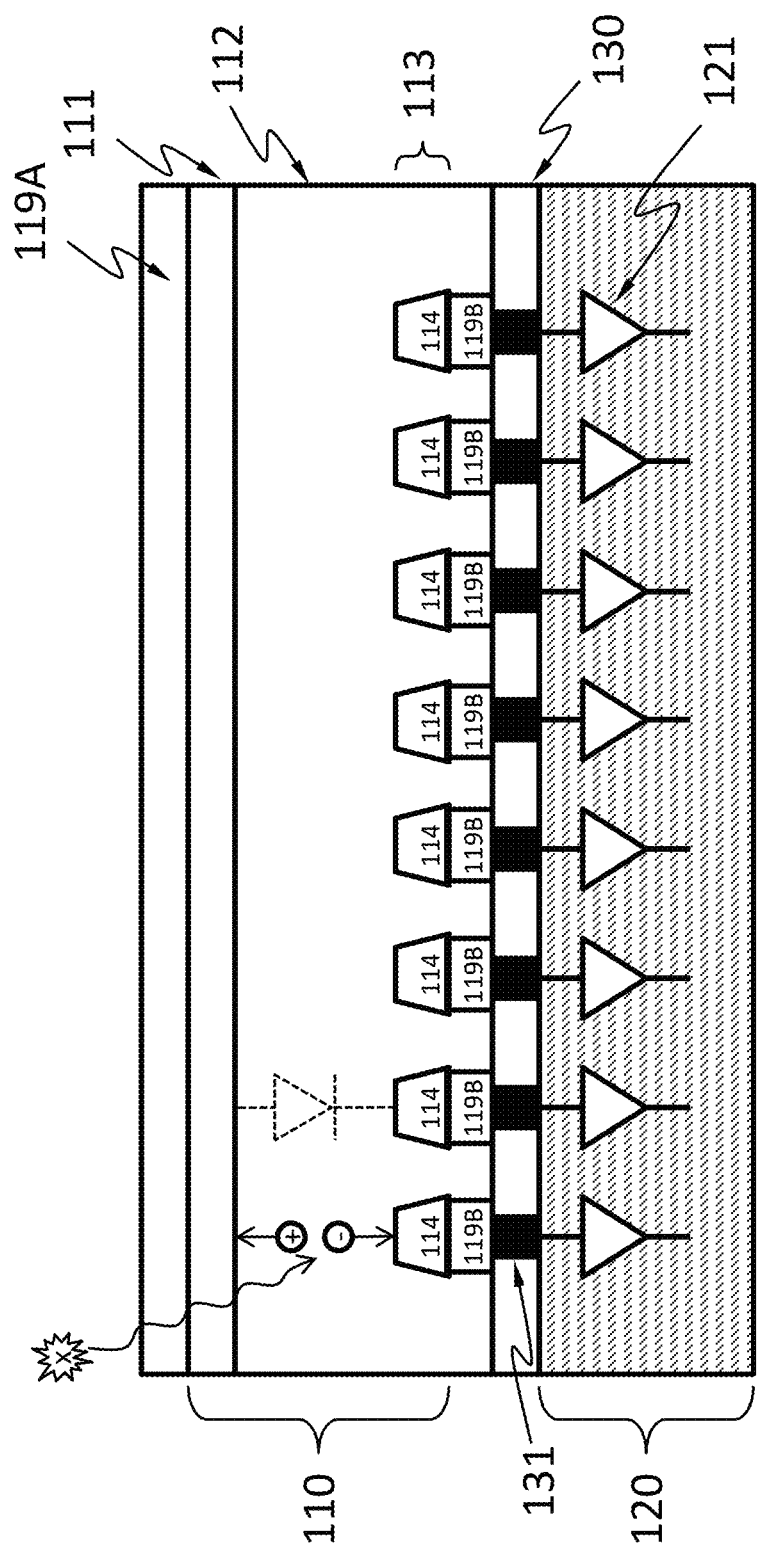
FIG. 1B schematically shows a detailed cross-sectional view of the detector, according to an embodiment.

As shown in a detailed cross-sectional view of the detector 100 in FIG. 1B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the X-ray absorption layer 110 has a plurality of diodes having the first doped region 111 as a shared electrode. The first doped region 111 may also have discrete portions.

When an X-ray photon hits the X-ray absorption layer 110 including diodes, the X-ray photon may be absorbed and generate one or more charge carriers by a number of mechanisms. An X-ray photon may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers generated by a single X-ray photon can be shared by two different discrete regions 114.

Figure 1C:
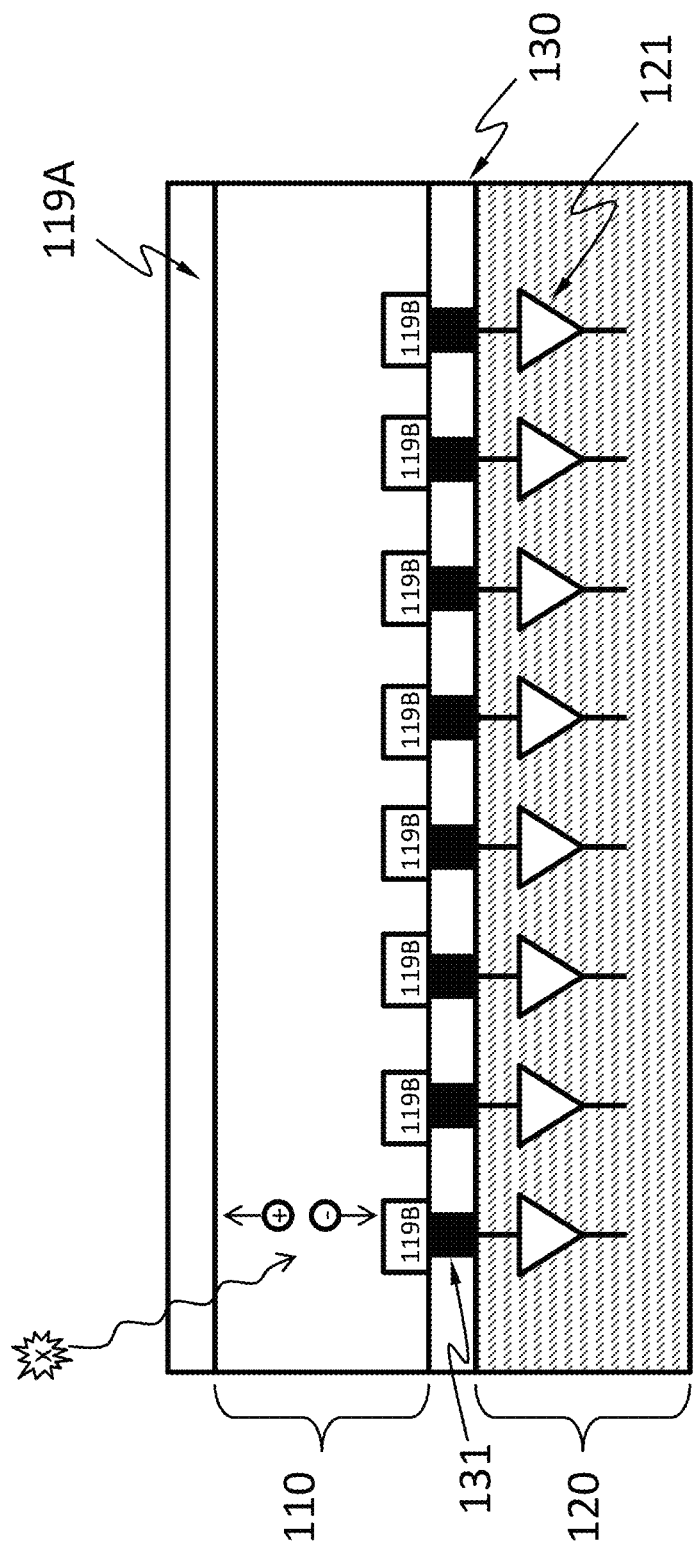
FIG. 1C schematically shows an alternative detailed cross-sectional view of the detector, according to an embodiment.

As shown in an alternative detailed cross-sectional view of the detector 100 in FIG. 1C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray energy of interest.

When an X-ray photon hits the X-ray absorption layer 110 including a resistor but not diodes, it may be absorbed and generate one or more charge carriers by a number of mechanisms. An X-ray photon may generate 10 to 100000 charge carriers. The charge carriers may drift to the electrical contacts 119A and 119B under an electric field. The field may be an external electric field. The electrical contact 119B includes discrete portions. In an embodiment, the charge carriers generated by a single X-ray photon can be shared by two different contacts 119B.

The electronics layer 120 may include an electronic system 121 suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessors, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131.

Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 2A:
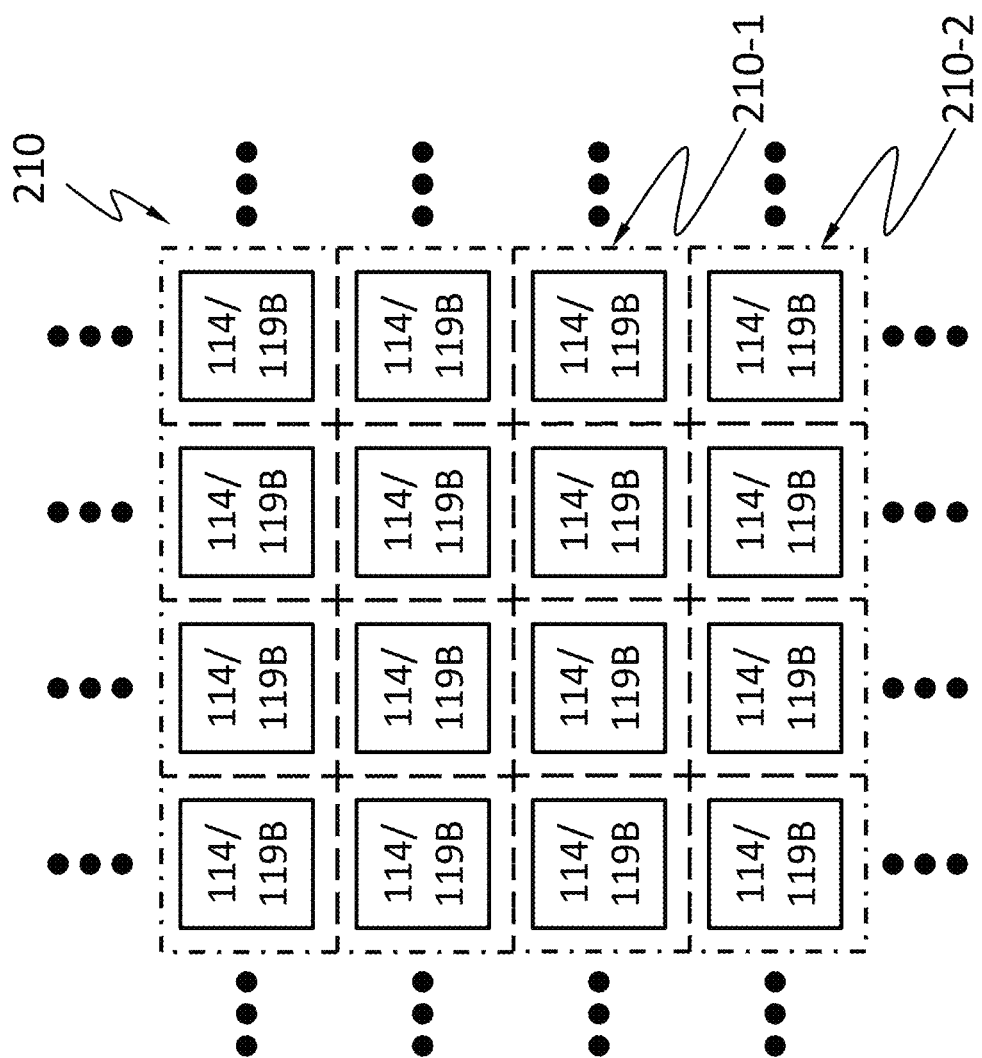
FIG. 2A shows an exemplary top view of a portion of a semiconductor X-ray detector, according to an embodiment.

FIG. 2A shows an exemplary top view of a portion of the device 100 with a 4-by-4 array of discrete regions 114. Charge carriers generated by an X-ray photon incident around the footprint of one of these discrete regions 114 are not substantially shared with another of these discrete regions 114. The area 210 around a discrete region 114 in which substantially all (more than 95%, more than 98% or more than 99% of) charge carriers generated by an X-ray photon incident therein flow to the discrete region 114 is called a pixel associated with that discrete region 114. Namely, less than 5%, less than 2% or less than 1% of these charge carriers flow beyond the pixel, when the X-ray photon hits inside the pixel. The pixels may be organized in any suitable array, such as, a square array, a triangular array and a honeycomb array. The pixels may have any suitable shape, such as, circular, triangular, square, rectangular, and hexangular. The pixels may be individually addressable.

Similarly, when the 4-by-4 array in FIG. 2A indicates an array of discrete portions of the electrical contact 119B in FIG. 1B, the charge carriers generated by an X-ray photon incident around the footprint of one of these discrete portions of the electrical contact 119B are not substantially shared with another of these discrete portions of the electrical contact 119B. The area around a discrete portion of the electrical contact 119B in which substantially all (more than 95%, more than 98% or more than 99% of) charge carriers generated by an X-ray photon incident therein flow to the discrete portion of the electrical contact 119B is called a pixel associated with the discrete portion of the electrical contact 119B. Namely, less than 5%, less than 2% or less than 1% of these charge carriers flow beyond the pixel associated with the one discrete portion of the electrical contact 119B, when the X-ray photon hits inside the pixel. The pixels may be organized in any suitable array, such as, a square array, a triangular array and a honeycomb array. The pixels may have any suitable shape, such as, circular, triangular, square, rectangular, and hexangular. The pixels may be individually addressable.

As shown in FIG. 2A, two pixels 210 (e.g. 210-1 and 210-2) associated with two neighboring discrete regions 114 can be called two neighboring pixels ("neighboring pixels" used in the present teaching means pixels that are close to each other such that carriers generated from a single photon may be shared by these pixels).

Figure 2B:
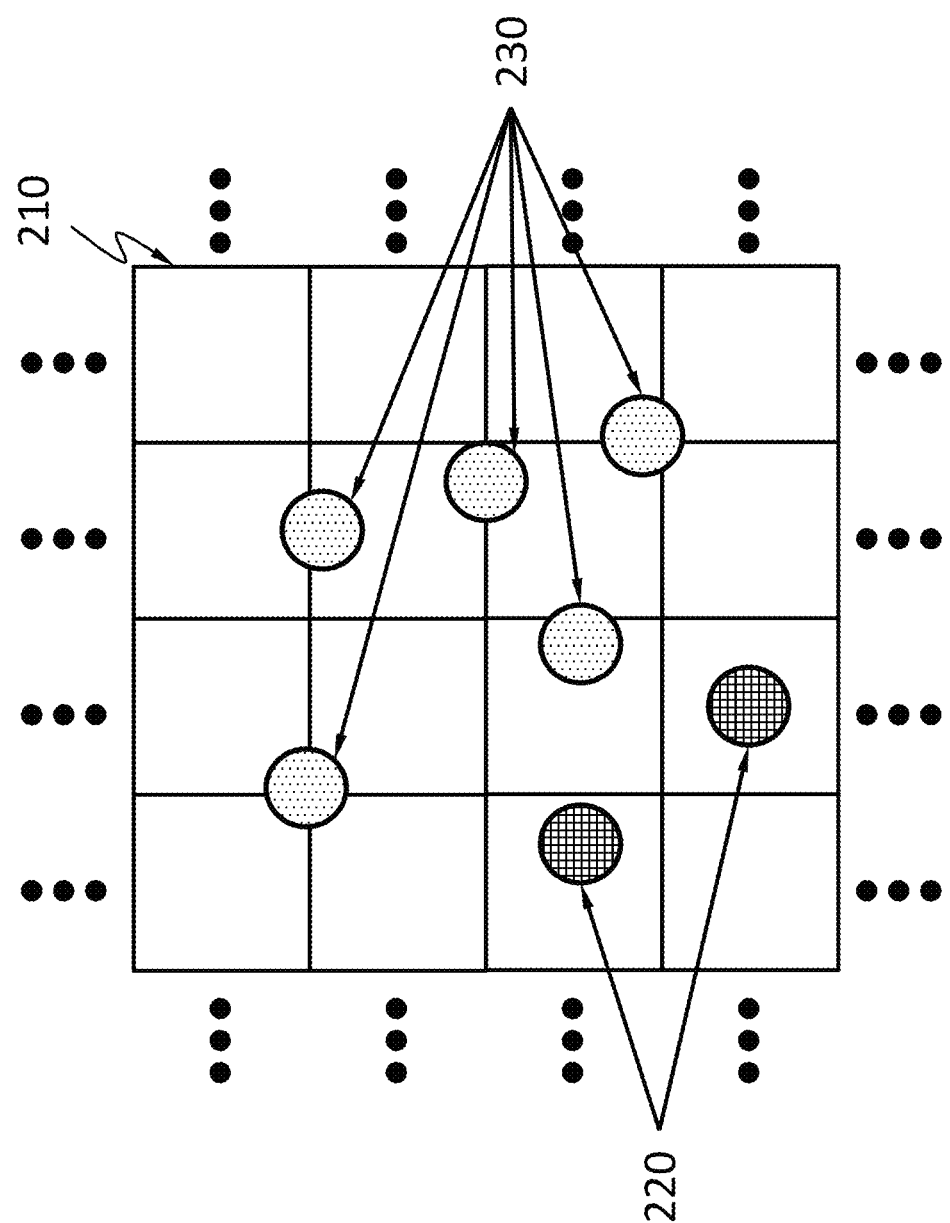
FIG. 2B shows an exemplary array of pixels in a semiconductor X-ray detector, according to an embodiment.

FIG. 2B shows an exemplary array of pixels in a semiconductor X-ray detector, according to an embodiment. When an X-ray photon hits the array, it may be absorbed and cause multiple charge carriers to be generated. The carriers may transport in various directions, e.g. drift along the direction of an electric field and diffuse in all directions. In FIG. 2B, each circle (e.g. 220, 230) represents the footprint of a transport area of charge carriers generated by a photon ("transport area" used in the present teaching means a space the carriers generated by a photon are transported into).

As shown in FIG. 2B, a transport area may sit inside a pixel (e.g. transport areas 220), or on a boundary of neighboring pixels (e.g. transport areas 230).

As discussed above, when a transport area sits on a boundary of two or more neighboring pixels, charge sharing occurs, which may cause issues for energy measurement. Charge sharing may also lead to errors in counting the number photons. In an embodiment, the electronic system 121 in an X-ray detector can still accurately measure the energy of an X-ray photon even if a charge sharing occurs to the carriers generated by the X-ray photon.

According to an embodiment, two neighboring pixels do not have to share a boundary, but can be close to each other such that carriers generated from a single photon may be shared by the two pixels. That is, charge sharing may occur on neighboring pixels, even if there is not a boundary shared by the neighboring pixels.

A size of a pixel can be determined by design, based on fabrication process. As shown in FIG. 2B, the size of each pixel is designed to be the same and enough to cover a transport area when the corresponding photon hits around the center of the pixel. If the size of a pixel is too small, e.g. smaller than a transport area, then charge sharing can happen all the time. On the other hand, if the size of a pixel is too large, it is very likely for multiple photons to hit the pixel at the same time, which can generate difficulty for accurate X-ray detection and image generation.

Figure 3A:
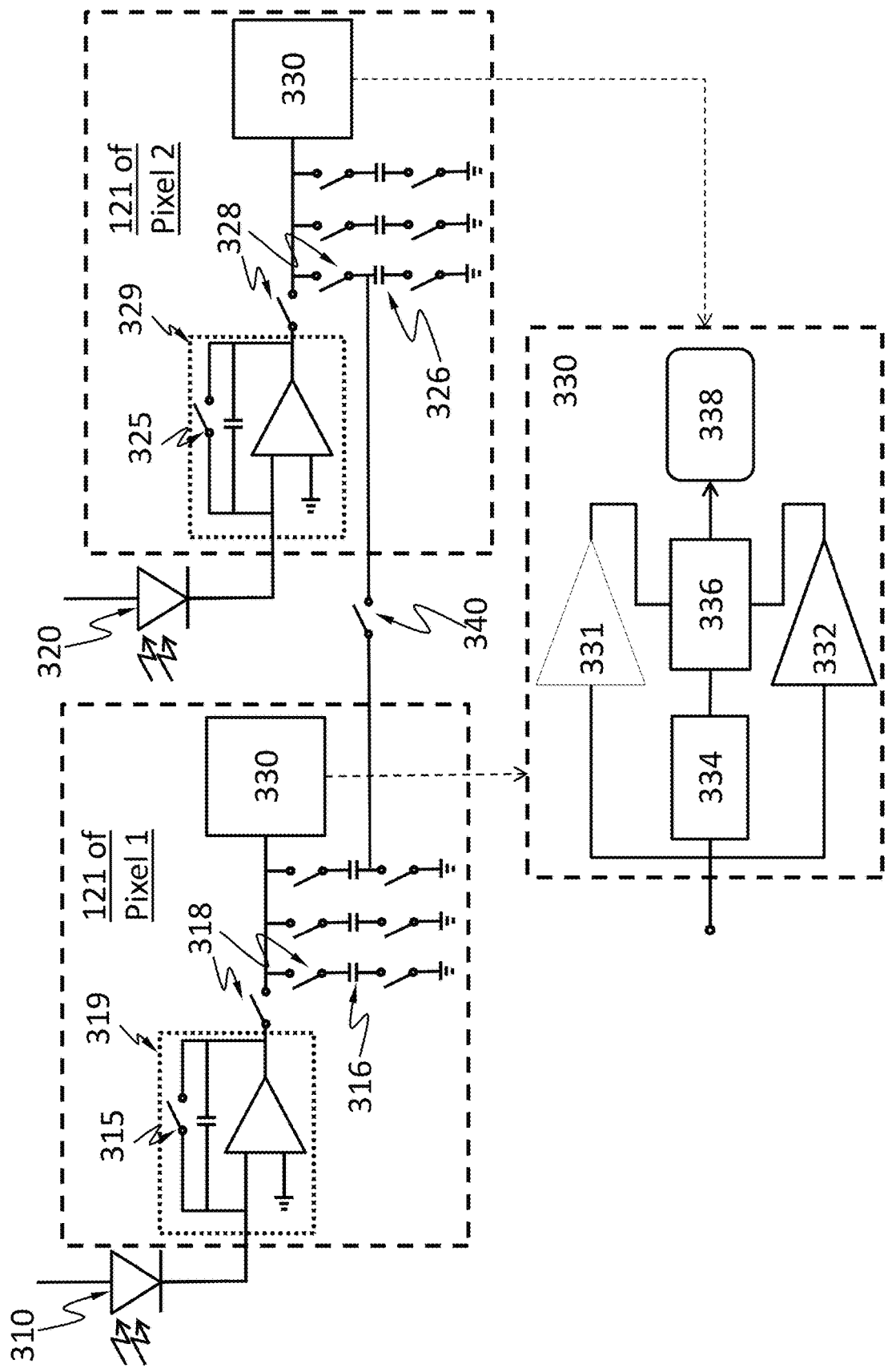
FIG. 3A shows component diagrams of two neighboring electronic systems of a semiconductor X-ray detector, according to an embodiment.

FIG. 3A shows component diagrams of two electronic systems 121 in two neighboring pixels of a semiconductor X-ray detector, according to an embodiment. In this example, Pixel 1 and Pixel 2 in FIG. 3A are two neighboring pixels of a semiconductor X-ray detector. As shown in FIG. 3A, the electronic system 121 of Pixel 1 is configured for processing signals from an electrode of a diode 310 in Pixel 1; and the electronic system 121 of Pixel 2 is configured for processing signals from an electrode of a diode 320 in Pixel 2.

Figure 4A:
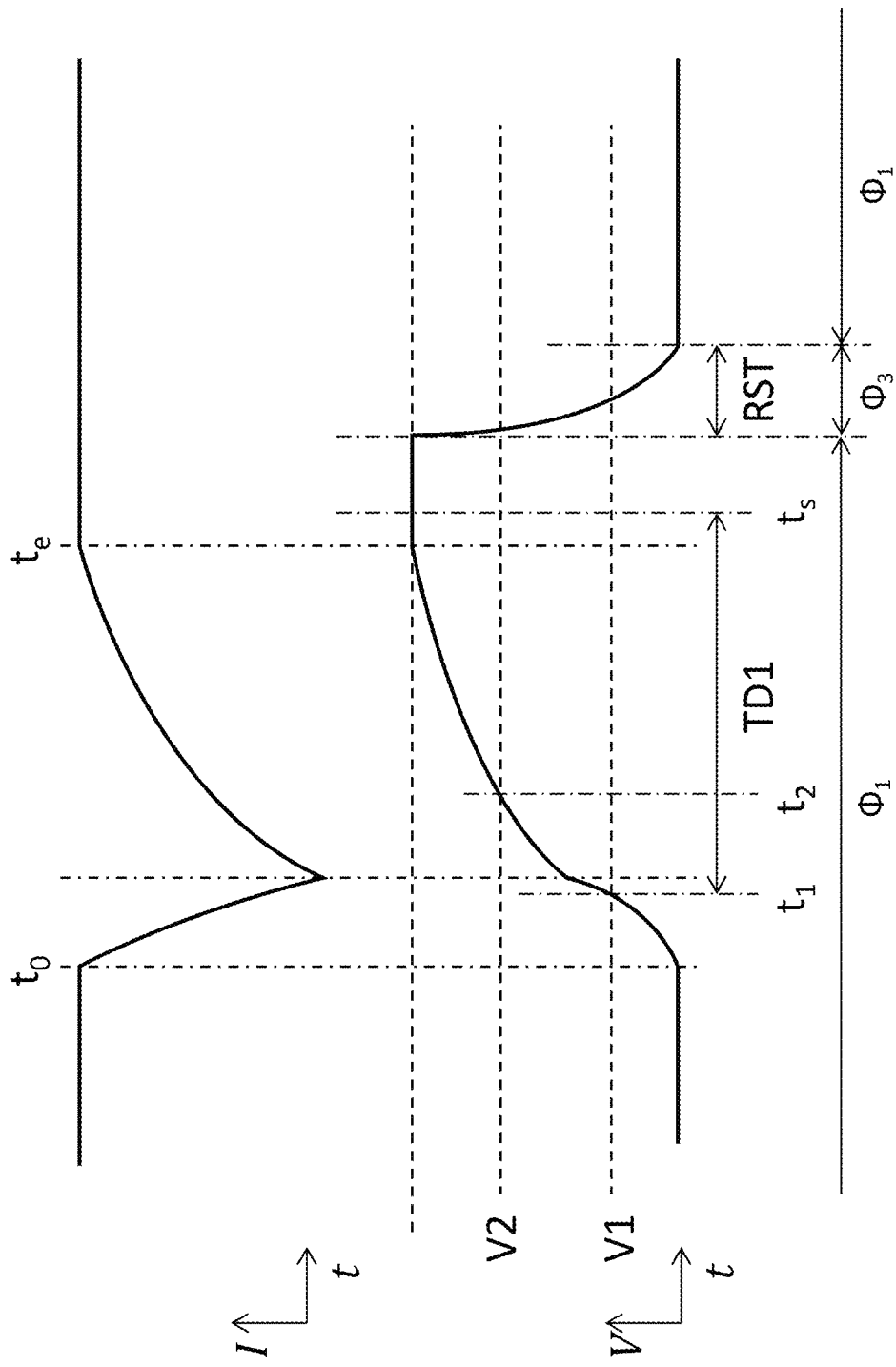
FIG. 4A schematically shows a temporal change of the electric current flowing through an electrode (upper curve) of a diode or an electrical contact of a resistor of an X-ray absorption layer exposed to X-ray, the electric current caused by charge carriers generated by an X-ray photon incident on the X-ray absorption layer, and a corresponding temporal change of the voltage of the electrode (lower curve), when no charge sharing occurs, according to an embodiment.

In this example, the electronic system 121 of Pixel 1 may include a capacitor module 319, one or more sampling capacitors 316, a plurality of control switches 318, and a data processing module 330. As shown in FIG. 3A, the capacitor module 319 is electrically connected to the electrode of the diode 310 or the electrical contact. The capacitor module 319 is configured to collect charge carriers from the electrode. The capacitor module 319 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode may accumulate on the capacitor over a period of time ("integration period") (e.g., as shown in FIG. 4A, between $t_0$ and $t_1$, or between $t_1$ and $t_2$). After the integration period has expired, the capacitor voltage is sampled and then reset by a reset switch 315. The capacitor module 319 can include a capacitor directly connected to the electrode.

When no charge sharing occurs, the plurality of control switches 318 are closed such that each of the one or more sampling capacitors 316 is charged with the voltage from the front end (diode and amplifier).

The electronic system 121 of Pixel 2 may include a same structure as the electronic system 121 of Pixel 1. As shown in FIG. 3A, the electronic system 121 of Pixel 2 may include a capacitor module 329, one or more sampling capacitors 326, a plurality of control switches 328, and a data processing module 330. The capacitor module 329 is electrically connected to the electrode of the diode 320 or the electrical contact. Similar to the capacitor module 319, the capacitor module 329 is configured to collect charge carriers from the electrode. The capacitor module 329 can include a capacitor in the feedback path of a CTIA. Charge carriers from the electrode may accumulate on the capacitor over a period of time ("integration period") (e.g., as shown in FIG. 4A, between $t_0$ and $t_1$, or between $t_1$ and $t_2$). After the integration period has expired, the capacitor voltage is sampled and then reset by a reset switch 325. The capacitor module 329 can include a capacitor directly connected to the electrode.

When no charge sharing occurs, the plurality of control switches 328 and the one or more sampling capacitors 326 may work in a same manner as the plurality of control switches 318 and the one or more sampling capacitors 316, respectively. When the plurality of control switches 328 are closed, each of the one or more sampling capacitors 316 is charged with the voltage from the front end (diode and amplifier).

Both of the two electronic systems 121 in FIG. 3A may comprise the data processing module 330 that may include downstream circuits for interpreting and processing signal from upstream of the electronic system 121.

According to an embodiment, the data processing module 330 includes a first voltage comparator 331, a second voltage comparator 332, a counter 338, a voltmeter 334 and a controller 336.

The first voltage comparator 331 is configured to compare a voltage (e.g. a voltage of an electrode or a diode 310 or 320) to a first threshold. The diode may be a diode formed by the first doped region 111, one of the discrete regions 114 of the second doped region 113, and the optional intrinsic region 112. Alternatively, the first voltage comparator 331 is configured to compare the voltage of an electrical contact (e.g., a discrete portion of electrical contact 119B) to a first threshold. The first voltage comparator 331 may be configured to monitor the voltage directly, or calculate the voltage by integrating an electric current flowing through the diode or electrical contact over a period of time. The first voltage comparator 331 may be controllably activated or deactivated by the controller 336. The first voltage comparator 331 may be a continuous comparator. Namely, the first voltage comparator 331 may be configured to be activated continuously, and monitor the voltage continuously. The first voltage comparator 331 configured as a continuous comparator reduces the chance that the system 121 misses signals generated by an incident X-ray photon. The first voltage comparator 331 configured as a continuous comparator is especially suitable when the incident X-ray intensity is relatively high. The first voltage comparator 331 may be a clocked comparator, which has the benefit of lower power consumption. The first voltage comparator 331 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 331 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 332 is configured to compare a voltage (e.g. a voltage of an electrode or a diode 310 or 320) to a second threshold. The second voltage comparator 332 may be configured to monitor the voltage directly, or calculate the voltage by integrating an electric current flowing through the diode or the electrical contact over a period of time. The second voltage comparator 332 may be a continuous comparator. The second voltage comparator 332 may be controllably activate or deactivated by the controller 336. When the second voltage comparator 332 is deactivated, the power consumption of the second voltage comparator 332 may be less than 1%, less than 5%, less than 10% or less than 20% of the power consumption when the second voltage comparator 332 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 332 and the first voltage comparator 310 may be the same component. Namely, the system 121 may have one voltage comparator that can compare a voltage with two different thresholds at different times.

The first voltage comparator 331 or the second voltage comparator 332 may include one or more op-amps or any other suitable circuitry. The first voltage comparator 331 or the second voltage comparator 332 may have a high speed to allow the system 121 to operate under a high flux of incident X-ray.

The counter 338 is configured to register a number of X-ray photons reaching a corresponding diode or resistor. The counter 338 may be a software component (e.g., a number stored in a computer memory) or a hardware component (e.g., a 4017 IC and a 7490 IC).

The controller 336 may be a hardware component such as a microcontroller and a microprocessor. The controller 336 may be configured to start a time delay from a time at which the first voltage comparator 331 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 336 may be configured to keep deactivated the second voltage comparator 332, the counter 338 and any other circuits the operation of the first voltage comparator 331 does not require, before the time at which the first voltage comparator 331 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 336 may be configured to activate the second voltage comparator during (including the beginning and the expiration) the time delay. In an embodiment, the controller 336 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 336 itself may be deactivated until the output of the first voltage comparator 331 activates the controller 336 when the absolute value of the voltage equals or exceeds the absolute value of the first threshold.

The controller 336 may be configured to cause the number registered by the counter 338 to increase by one, if, during the time delay, the second voltage comparator 332 determines that the absolute value of the voltage equals or exceeds the absolute value of the second threshold.

The controller 336 may be configured to cause the voltmeter 334 to measure the voltage upon expiration of the time delay. The controller 336 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 336 may connect the electrode to the electrical ground by controlling the reset switch 315 or 325. The switch may be a transistor such as a field-effect transistor (FET).

In an embodiment, the system 121 has no analog filter network (e.g., a RC network). In an embodiment, the system 121 has no analog circuitry.

The voltmeter 334 may feed the voltage it measures to the controller 336 as an analog or digital signal.

When no charge sharing occurs on Pixel 1 and Pixel 2, the two electronic systems 121 may operate independently and process signals generated from their respective corresponding electrodes of diodes (310 or 320). When no charge sharing occurs on Pixel 1 and Pixel 2, the plurality of control switches 318 are closed such that the voltage from the front end (diode and amplifier) is reflected on the sampling capacitors and measured by the data processing module 330. The same voltage may also be compared with a threshold by the data processing module 330 (e.g., using the first voltage comparator 331 and/or the second voltage comparator 332).

When no charge sharing occurs, after the rate of change of the voltage becomes substantially zero, the voltage is proportional to the amount of charge carriers generated by an X-ray photon, which relates to the energy of the X-ray photon. However, when charge sharing occurs on Pixel 1 and Pixel 2, the voltage measured by either of the two electronic systems 121 in FIG. 3A is not enough to estimate the amount of charge carriers generated by the X-ray photon. Therefore, some method is needed to estimate the energy of the X-ray photon, when charge sharing occurs. In one embodiment, there may be a shared switch 340 connecting the two electronic systems 121 of Pixel 1 and Pixel 2. The shared switch 340 may be used to serialize the sampling capacitors 316 and 326 from the two pixels. Detailed use of the shared switch 340 will be described with respect to FIG. 3B.

Figure 3B:
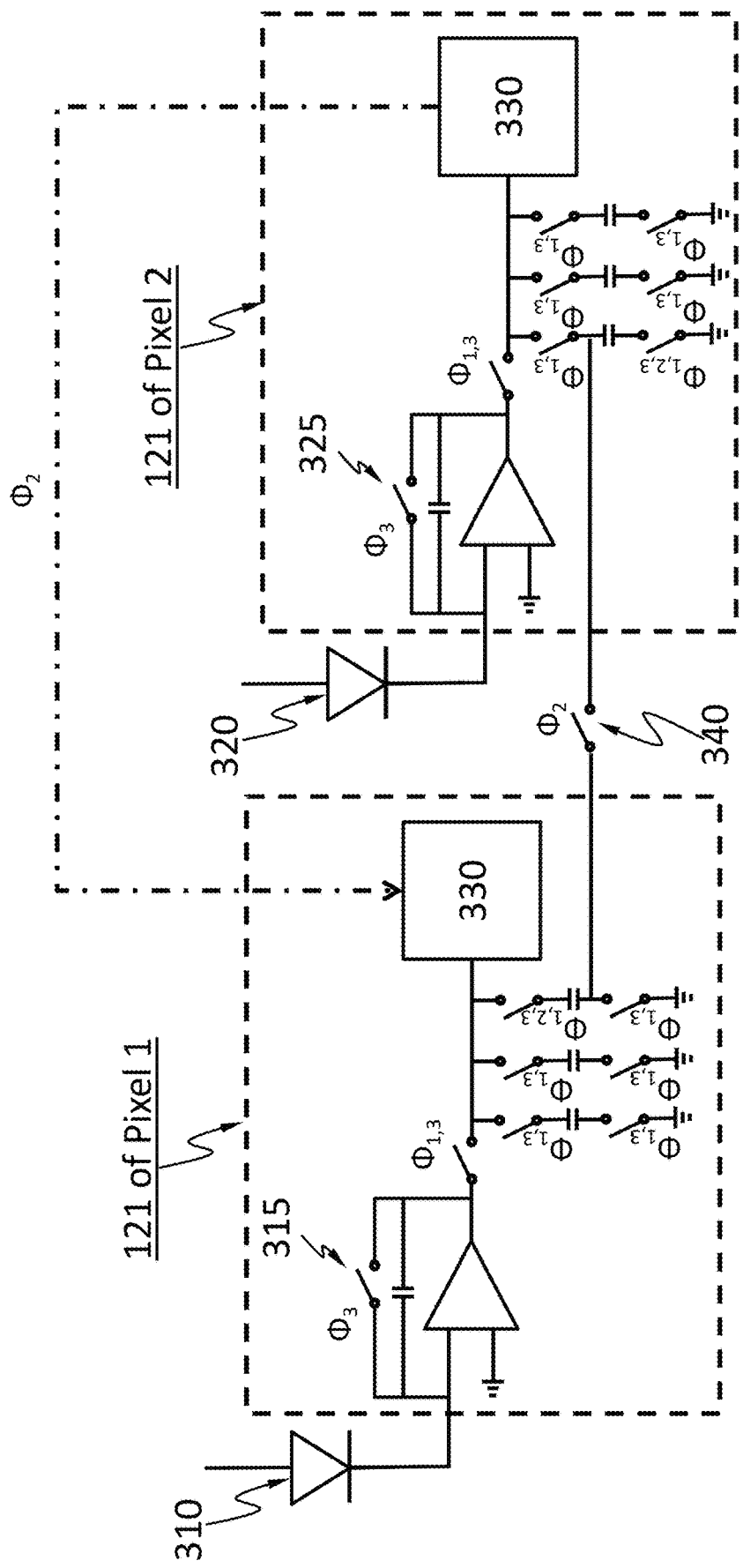
FIG. 3B shows component diagrams of two neighboring electronic systems of a semiconductor X-ray detector, with positions of switches marked when charge sharing occurs, according to an embodiment.

FIG. 3B shows component diagrams of two neighboring electronic systems of a semiconductor X-ray detector, with positions of switches marked, according to an embodiment. Similar to FIG. 3A, Pixel 1 and Pixel 2 in FIG. 3B are two neighboring pixels of a semiconductor X-ray detector. The electronic systems 121 of Pixel 1 and Pixel 2 in FIG. 3B have the same structure as the electronic systems 121 of Pixel 1 and Pixel 2, respectively in FIG. 3A. In addition, positions of the switches in FIG. 3B are marked according to different phases of the electronic systems 121's operation, which will be described in detail below.

In this example, a single X-ray photon may hit on a common boundary of the two neighboring pixels or on an area between the two neighboring pixels, and thus cause charge carriers generated and transported into both pixels. In this case, each of the diodes 310 and 320 may have a voltage increase caused by a portion of the charge carriers.

In this example, the two electronic systems 121 operate in different phases: phase 1 ($\Phi 1$), phase 2 ($\Phi 2$), and phase 3 ($\Phi 3$). The switch marked with $\Phi_2$ is closed only during phase 2. The switches marked with $\Phi_3$ are closed only during phase 3. The switches marked with $\Phi_{1,2,3}$ are closed during phase 1, phase 2 and phase 3. The switches marked with $\Phi_{1,3}$ are closed during phase 1 and phase 3.

The two pixels may be in phase 1 when they are ready to detect photons, where all switches except the shared switch 340 are closed. The two electronic systems 121 may cooperate either by communicating directly to each other or by a central controller controlling all pixels of the X-ray detector. Based on their cooperation, the two systems 121 can determine that charge sharing occurs on the two pixels, e.g. when they see voltages of the diodes 310 and 320 changed by charge carriers at the same time or in a same time period. Because the two pixels are in phase 1, where all switches except the shared switch 340 are closed, the voltage from the front end (diode and amplifier) is reflected on the sampling capacitors in each of the two electronic systems 121.

Since each voltage measured at one of the two pixels can only represent a portion of the energy of the X-ray photon, the two voltages may be added together to estimate the energy of the photon. The two electronic systems 121 then enter phase 2 to perform adding the two voltages.

According to an embodiment, in phase 2, the switches marked with $\Phi_2$ and $\Phi_{1,2,3}$ are closed, while the other switches are open. As shown in FIG. 3B, a sampling capacitor in Pixel 1 and a sampling capacitor in Pixel 2 are serially connected in phase 2, such that a voltage across the two serially connected capacitors equals to a sum of the two voltages of the two diodes excited by the same X-ray photon. A positive end of one of the two sampling capacitors is connected to a negative end of the other sample capacitor, such that their respective voltages are added together, i.e. an absolute value of the voltage across the two serially connected capacitors equals to a sum of the absolute values of the two voltages of the two diodes excited by the same X-ray photon.

During phase 2, the data processing module 330 in one of the two pixels (e.g. Pixel 1) can measure an absolute value of the sum and compare it with a threshold to determine to increase the number of absorbed photons by one, if the absolute value of the sum equals or exceeds the threshold. The energy of the photon can also be measured based on the sum of the voltages. In case charge sharing occurs on more than two pixels, more than two sampling capacitors, each of which is from one of the pixels, can be serially connected to obtain a sum voltage for measuring energy of an X-ray photon.

According to another embodiment, in phase 2, instead of connecting sampling capacitors, the two 330 may communicate with each other to numerically add the two voltages of the two diodes excited by the same X-ray photon. The communication between the two pixels may be via a central controller, a bus line, or any other suitable communication manner. In this case, no sampling capacitor is needed in any of the pixels; and no shared switch 340 is needed either.

After the energy is measured, the two pixels may enter phase 3, where the switches marked with $\Phi_{1,3}$ are closed, and the other switches are open. During phase 3, capacitor voltage is reset by a reset switch 315 or 325. According to an embodiment, the two pixels may reset their voltages at the same time or at different times. Accordingly, the two pixels may enter phase 3 at the same time or at different times.

After phase 3, the two pixels may enter phase 1 again, such that they are ready to measure next incident photon.

FIG. 4A schematically shows a temporal change of the electric current flowing through an electrode (upper curve) of a diode or an electrical contact of a resistor of an X-ray absorption layer exposed to X-ray, the electric current caused by charge carriers generated by an X-ray photon incident on the X-ray absorption layer, and a corresponding temporal change of the voltage of the electrode (lower curve), when no charge sharing occurs, according to an embodiment. The electrode may be either the diode 310 or 320 as shown in FIG. 3A and FIG. 3B, when no charge sharing occurs on the two pixels.

The voltage of the electrode may be an integral of the electric current with respect to time. As discussed above, a pixel is in phase 1 when it is ready to detect an X-ray photon. During phase 1, at time $t_0$, the X-ray photon hits the diode or the resistor, charge carriers start being generated in the diode or the resistor, electric current starts to flow through the electrode of the diode or the resistor, and the absolute value of the voltage of the electrode or electrical contact starts to increase. At time $t_1$, the first voltage comparator 331 determines that the absolute value of the voltage equals or exceeds the absolute value of the first threshold V1, and the controller 336 starts the time delay TD1 and the controller 336 may deactivate the first voltage comparator 331 at the beginning of TD1. If the controller 336 is deactivated before $t_1$, the controller 336 is activated at $t_1$. During TD1, the controller 336 activates the second voltage comparator 332. The term "during" a time delay as used here means the beginning and the expiration (i.e., the end) and any time in between. For example, the controller 336 may activate the second voltage comparator 332 at the expiration of TD1. If during TD1, the second voltage comparator 332 determines that the absolute value of the voltage equals or exceeds the absolute value of the second threshold at time $t_2$, the controller 336 causes the number registered by the counter 338 to increase by one. At time $t_e$, all charge carriers generated by the X-ray photon drift out of the X-ray absorption layer 110. At time $t_s$, the time delay TD1 expires. In the example of FIG. 4A, time $t_s$ is after time $t_e$; namely TD1 expires after all charge carriers generated by the X-ray photon drift out of the X-ray absorption layer 110. The rate of change of the voltage is thus substantially zero at $t_s$. The controller 336 may be configured to deactivate the second voltage comparator 332 at expiration of TD1 or at $t_2$, or any time in between.

The controller 336 may be configured to cause the voltmeter 334 to measure the voltage upon expiration of the time delay TD1. In an embodiment, the controller 336 causes the voltmeter 334 to measure the voltage after the rate of change of the voltage becomes substantially zero after the expiration of the time delay TD1. When no charge sharing occurs, the voltage at this moment is proportional to the amount of charge carriers generated by an X-ray photon, which relates to the energy of the X-ray photon. The controller 336 may be configured to determine the energy of the X-ray photon based on voltage the voltmeter 334 measures. One way to determine the energy is by binning the voltage. The counter 338 may have a sub-counter for each bin. When the controller 336 determines that the energy of the X-ray photon falls in a bin, the controller 336 may cause the number registered in the sub-counter for that bin to increase by one. Therefore, the system 121 may be able to detect an X-ray image and may be able to resolve X-ray photon energies of each X-ray photon.

After TD1 expires, the controller 336 connects the electrode to an electric ground for a reset period RST to allow charge carriers accumulated on the electrode to flow to the ground and reset the voltage. After the expiration of TD1 and before the reset period RST, the pixel may end phase 1 and enter phase 3. Because there is no charge sharing in this example, the pixel does not need phase 2 for voltage adding.

After RST, the system 121 enters phase 1 again and is ready to detect another incident X-ray photon. Implicitly, the rate of incident X-ray photons the system 121 can handle in the example of FIG. 4A is limited by 1/(TD1+RST). If the first voltage comparator 331 has been deactivated, the controller 336 can activate it at any time before RST expires. If the controller 336 has been deactivated, it may be activated before RST expires.

Figure 4B:
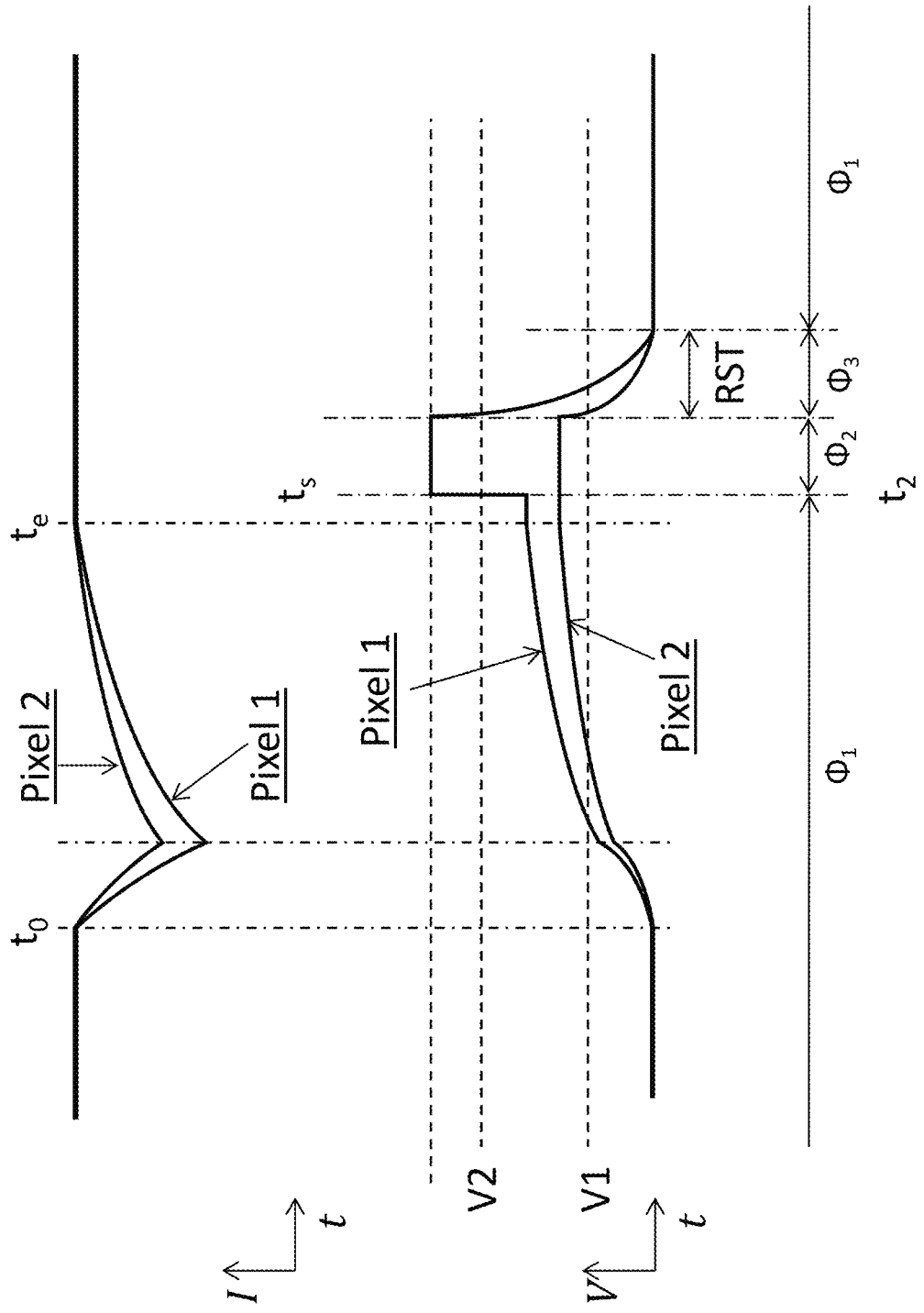
FIG. 4B schematically shows temporal changes of the electric currents flowing through two neighboring electrodes (upper curves) and corresponding temporal changes of the voltages of the electrodes (lower curves), when charge sharing occurs, according to an embodiment. Each electrode may be an electrical contact of a diode or a resistor of an X-ray absorption layer exposed to X-ray. The electric currents are caused by charge carriers generated by an X-ray photon incident on the X-ray absorption layer.

FIG. 4B schematically shows temporal changes of the electric currents flowing through two neighboring electrodes (upper curves) and corresponding temporal changes of the voltages of the electrodes (lower curves), when charge sharing occurs, according to an embodiment. Each electrode may be a diode or an electrical contact of a resistor of an X-ray absorption layer exposed to X-ray. The electric currents are caused by charge carriers generated by an X-ray photon incident on the X-ray absorption layer. The two electrodes may be diodes 310 and 320 shown in FIG. 3A and FIG. 3B, when charge sharing occurs on the two pixels.

The voltage of each electrode may be an integral of the corresponding electric current with respect to time. As discussed above, the two pixels (Pixel 1 and Pixel 2) are in phase 1 when they are ready to detect an X-ray photon. During phase 1, at time $t_0$, the X-ray photon hits in an area near a boundary of or between two neighboring pixels including the two diodes 310 and 320 or two resistors, charge carriers start being generated in the diodes or the resistors, electric current starts to flow through the electrodes of the diodes or the resistors, and the absolute value of each of the two voltages of the electrodes or electrical contacts starts to increase. Then, the two pixels determine that charge sharing occurs at the two pixels.

According to an embodiment, if the time points at which the absolute values of the two voltages start to increase differ by less than a given amount (e.g., 10 μs, 1 μs, 100 ns, or 10 ns), charge sharing is considered to occur between these two pixels.

As shown in FIG. 4B, the two pixels may have different increasing rates of the voltages and/or currents, because the amount of charge carriers transporting into the two pixels may be different. Accordingly, during phase 1, the two voltages may reach the first threshold V1 at different times. In one embodiment, one of the two voltages does not reach the first threshold V1 during phase 1. In one embodiment, at least one of the two voltages reaches the second threshold V2 during phase 1.

In another embodiment, the two pixels independently determine whether a photon hits them. If the voltage on one pixel reaches V1, determine whether the voltage on that pixel exceeds V2 within a delay. If the voltages on both pixels exceeds V2 roughly at the same time (i.e., within a given time difference), it is considered that charge sharing occurs between these two pixels.

In another embodiment, the two pixels independently determine whether a photon hits them. If the voltages of the pixels reach V1 roughly at the same time (i.e., within a given time difference), and the voltage of at least one of the pixels reaches V2 within a delay, it is considered that charge sharing occurs between these two pixels.

In an embodiment, V2 can be set to a value corresponding to ½ to ¼ of the energy of the incident X-ray photons.

In an embodiment, when the voltage of a pixel starts to rise, or reaches V1, or reaches V2, as the case may be, the pixel may set an indicator indicating that fact. A logic circuit may determine the time difference between the indicators of neighboring pixels and determine whether charge sharing occurs and between which pixels charge sharing occurs, based on the time difference.

In an embodiment, when the voltage of a pixel passes V2 and the voltage of any neighboring pixel has already reached V1 by that time, charge sharing can be considered to have already occurred.

As discussed above, when charge sharing occurs at the two pixels, either voltage measured at one of the two pixels cannot represent the energy of the X-ray photon. Therefore, if it is determined that charge sharing occurs at the two pixels, the sum of the voltages measured on these pixels after the voltages are stable may be used to derive the energy of the X-ray photon. The voltage at a pixel is stable when the rate of change of the voltage is substantially zero (e.g., rate of change less than 1%/ns) for a time period, e.g. 1 ms or 0.1 ms. For two pixels that share charges generated by a single photon, their voltages can stabilize roughly at the same time.

Phase 1 may end at or after the stabilization of the voltages at the two pixels. In the example of FIG. 4B, at time $t_e$, all charge carriers generated by the X-ray photon drift out of the X-ray absorption layer 110. As such, the rate of change of the voltage at each pixel may be substantially zero after $t_e$. Here, at time $t_s$ after $t_e$, phase 1 ends and the two pixels enter phase 2.

During phase 2, the voltage detected at Pixel 2 is added to the voltage detected at Pixel 1, either by capacitor serial connection or by numerical adding. If during phase 2, the second voltage comparator 332 of Pixel 1 determines that the absolute value of the added voltage equals or exceeds the absolute value of the second threshold, the controller 336 of Pixel 1 causes the number registered by the counter 338 of Pixel 1 to increase by one.

The controller 336 of Pixel 1 may be configured to cause the voltmeter 334 of Pixel 1 to measure the added voltage during phase 2. In an embodiment, the controller 336 of Pixel 1 causes the voltmeter 334 of Pixel 1 to measure the added voltage after the rate of change of the voltage becomes substantially zero during phase 2. When charge sharing caused by an X-ray photon occurs at Pixel 1 and Pixel 2, the added voltage at this moment is proportional to the amount of charge carriers generated by the X-ray photon, which relates to the energy of the X-ray photon. The controller 336 of Pixel 1 may be configured to determine the energy of the X-ray photon based on voltage the voltmeter 334 of Pixel 1 measures. One way to determine the energy is by binning the voltage. The counter 338 of Pixel 1 may have a sub-counter for each bin. When the controller 336 of Pixel 1 determines that the energy of the X-ray photon falls in a bin, the controller 336 of Pixel 1 may cause the number registered in the sub-counter for that bin to increase by one. Therefore, the system 121 may be able to detect an X-ray image and may be able to resolve X-ray photon energies of each X-ray photon, even if charge sharing occurs.

After the added voltage is obtained, the two pixels may end phase 2 and enter phase 3. During phase 3, each controller 336 connects the electrode to an electric ground for a reset period RST to allow charge carriers accumulated on the electrode to flow to the ground and reset the voltage.

After RST, each system 121 enters phase 1 again and is ready to detect another incident X-ray photon.

Figure 5A:
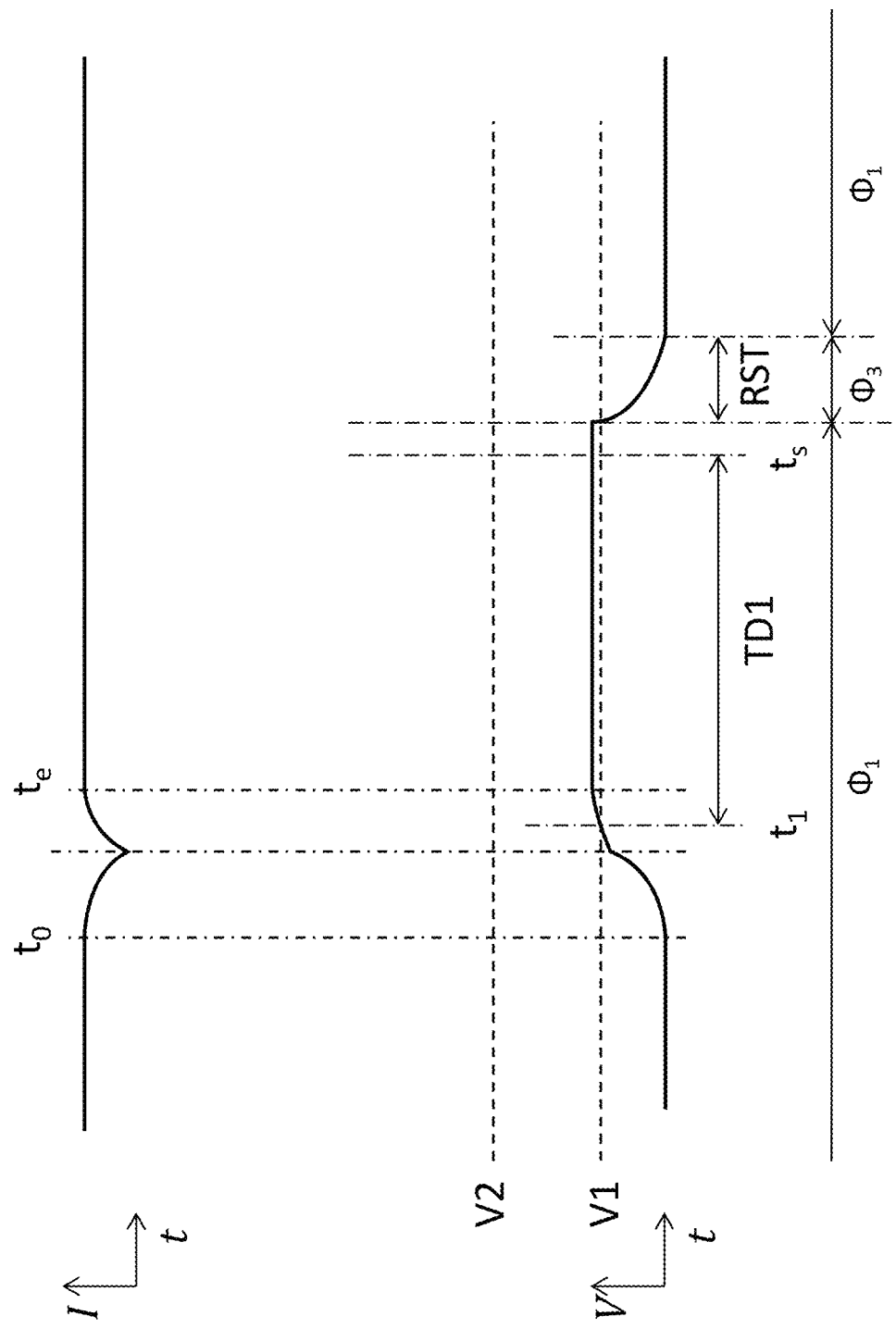
FIG. 5A schematically shows a temporal change of the electric current flowing through the electrode (upper curve) caused by noise (e.g., dark current), and a corresponding temporal change of the voltage of the electrode (lower curve), in the electronic system operating in the way shown in FIG. 4A, according to an embodiment.

FIG. 5A schematically shows a temporal change of the electric current flowing through the electrode (upper curve) caused by noise, and a corresponding temporal change of the voltage of the electrode (lower curve), in the electronic system operating in the way shown in FIG. 4A, according to an embodiment. The electrode may be either the diode 310 or 320 as shown in FIG. 3A and FIG. 3B. During phase 1, at time $t_0$, the noise begins. If the noise is not large enough to cause the absolute value of the voltage to exceed the absolute value of V1, the controller 336 does not activate the second voltage comparator 332. If the noise is large enough to cause the absolute value of the voltage to exceed the absolute value of V1 at time $t_1$ as determined by the first voltage comparator 331, the controller 336 starts the time delay TD1 and the controller 336 may deactivate the first voltage comparator 331 at the beginning of TD1. During TD1 (e.g., at expiration of TD1), the controller 336 activates the second voltage comparator 332. The noise is very unlikely large enough to cause the absolute value of the voltage to exceed the absolute value of V2 during TD1. Therefore, the controller 336 does not cause the number registered by the counter 338 to increase. At time $t_e$, the noise ends. At time $t_s$, the time delay TD1 expires. The controller 336 may be configured to deactivate the second voltage comparator 332 at expiration of TD1. The controller 336 may be configured not to cause the voltmeter 334 to measure the voltage if the absolute value of the voltage does not exceed the absolute value of V2 during TD1.

After TD1 expires, the pixel ends phase 1 and enters phase 3 directly because it did not determine that charge sharing occurred. During phase 3, the controller 336 connects the electrode to an electric ground for a reset period RST to allow charge carriers accumulated on the electrode as a result of the noise to flow to the ground and reset the voltage. Therefore, the system 121 may be very effective in noise rejection.

Figure 5B:
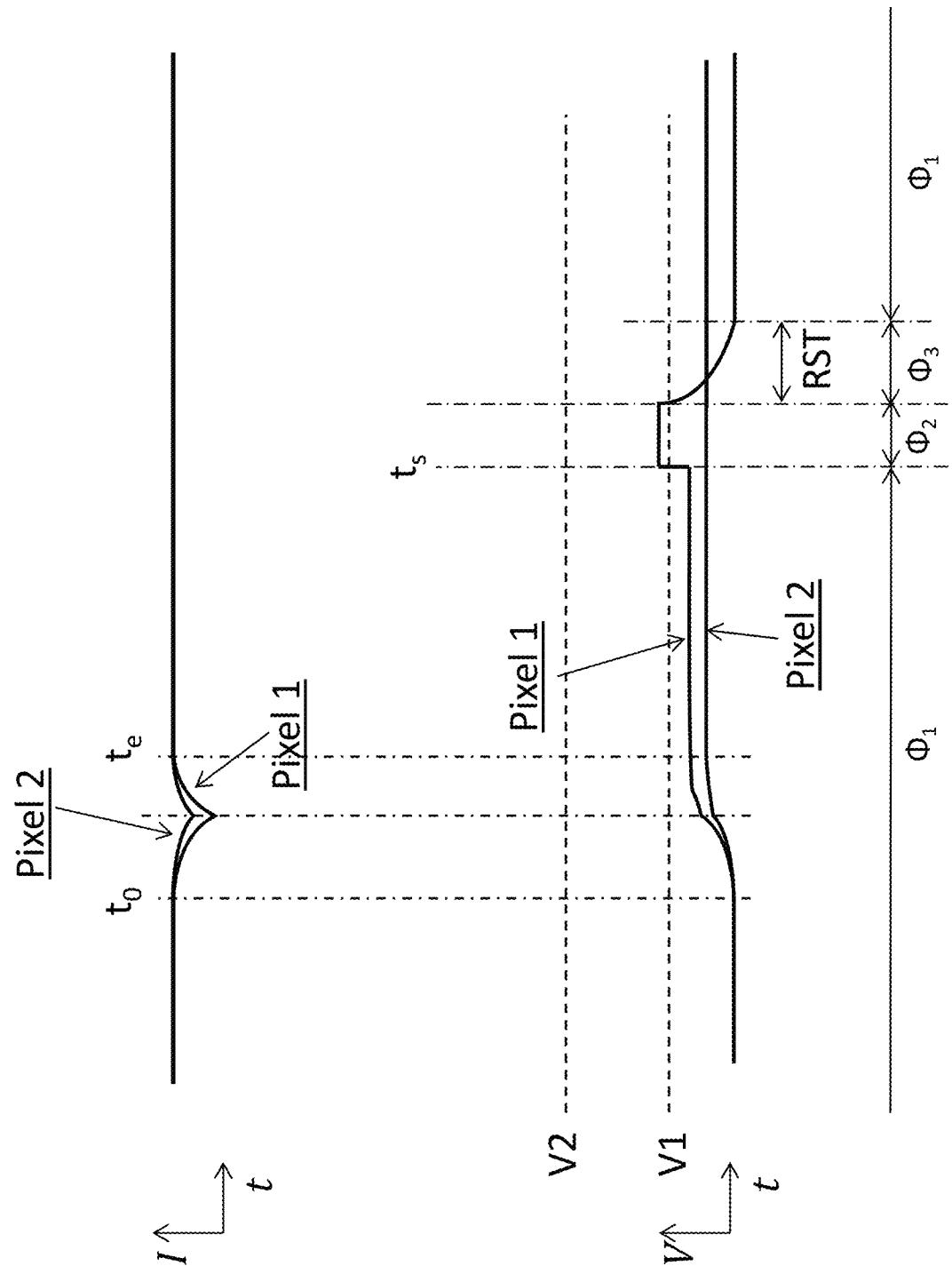
FIG. 5B schematically shows temporal changes of the electric currents flowing through the two neighboring electrodes (upper curves) caused by noise (e.g., dark current), and corresponding temporal changes of the voltages of the electrodes (lower curves), in the electronic system operating in the way shown in FIG. 4B, according to an embodiment.

FIG. 5B schematically shows temporal changes of the electric currents flowing through the two neighboring electrodes (upper curves) caused by noise, and corresponding temporal changes of the voltages of the electrodes (lower curves), in the electronic system operating in the way shown in FIG. 4B, according to an embodiment. In this example, during phase 1, noises begin at the two neighboring pixels (Pixel 1 and Pixel 2) at the same time $t_0$, or within a same time period. Thus, the two pixels cooperate as in the process of FIG. 4B.

As discussed above, phase 1 may end after the rates of changes of the voltages are substantially zero at both pixels. In the example of FIG. 5B, at time $t_e$, the noises end. As such, the rate of change of the voltage at each pixel may be substantially zero after $t_e$. Here, at time $t_s$ after $t_e$, phase 1 ends and the two pixels enter phase 2.

During phase 2, the voltage detected at Pixel 2 is added to the voltage detected at Pixel 1, either by capacitor serial connection or by numerical adding. In this example, the controller 336 of Pixel 1 activates the second voltage comparator 332 of Pixel 1, after Pixel 1 determines that charge sharing occurs, after voltage stabilization of the two pixels, or after phase 2 starts. The noise is very unlikely large enough to cause the absolute value of the added voltage to exceed the absolute value of V2, where the probability of having two noises simultaneously at two neighboring pixel is already very low. Therefore, the controller 336 of Pixel 1 does not cause the number registered by the counter 338 of Pixel 1 to increase. Each controller 336 may be configured to deactivate the second voltage comparator 332 at the end of phase 2. Each controller 336 may be configured not to cause the voltmeter 334 to measure the voltage if the absolute value of the voltage (or added voltage) does not exceed the absolute value of V2 during phase 2.

After the added voltage is obtained, the two pixels may end phase 2 and enter phase 3. During phase 3, each controller 336 connects the electrode to an electric ground for a reset period RST to allow charge carriers accumulated on the electrode as a result of the noise to flow to the ground and reset the voltage. Therefore, the systems 121 may be very effective in noise rejection, even if voltage adding is activated for potential charge sharing management.

According to another embodiment, whether charge sharing occurs at two pixels may be determined using the time when the absolute values of the voltages equal or exceed the absolute value of the first threshold V1. If the absolute values of the two voltages reach the first threshold within a same time period, e.g. 10 μs, 1 μs, 100 ns, or 10 ns, charge sharing may be considered occurring at the two pixels. This decision strategy may help to reject a concurrent noise at a neighboring pixel, when a photon hits inside a given pixel.

Figure 6:
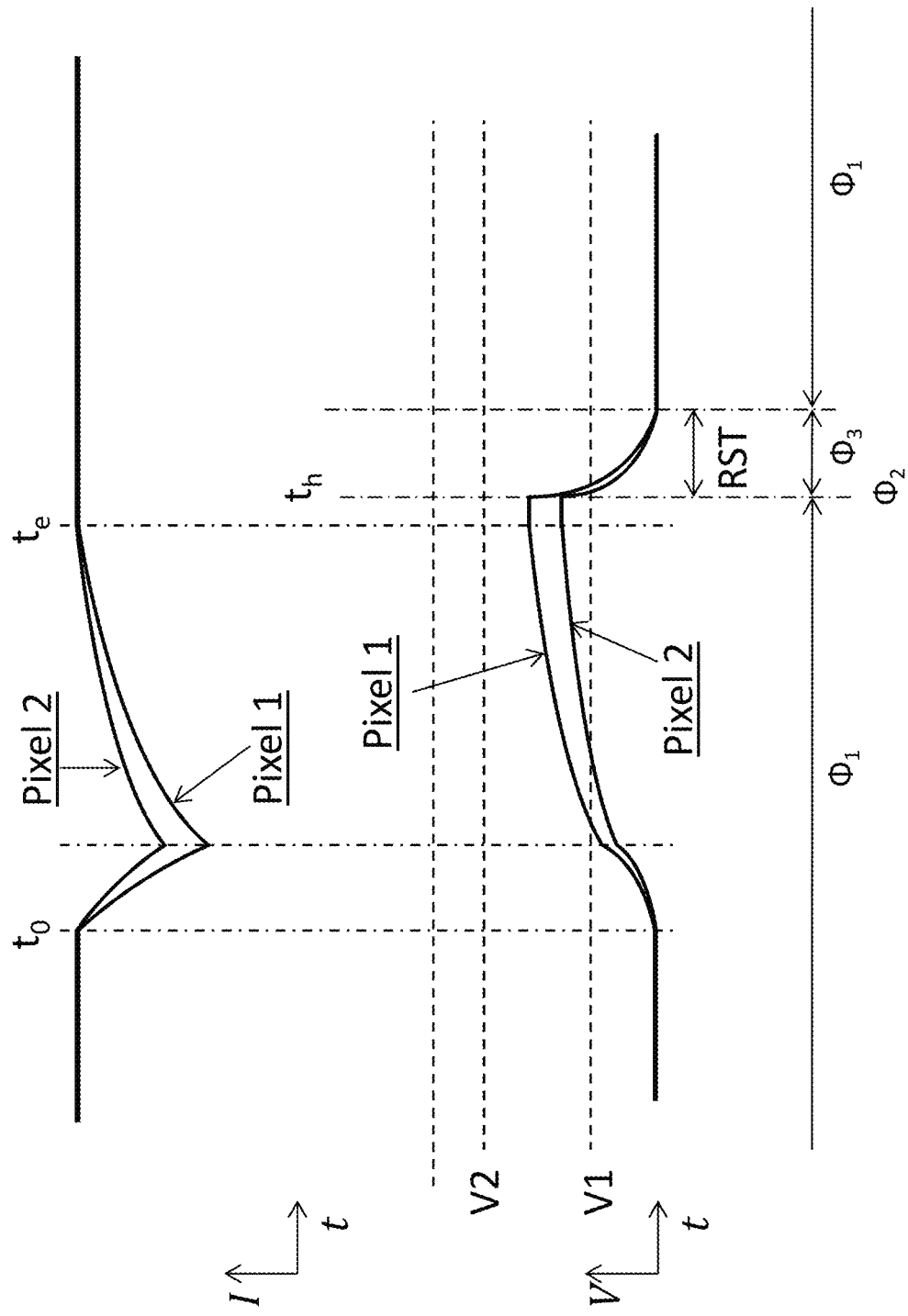
FIG. 6 schematically shows temporal changes of the electric currents flowing through two neighboring electrodes (upper curves) of the X-ray absorption layer exposed to X-ray, the electric currents caused by charge carriers generated by an X-ray photon incident on the X-ray absorption layer, and corresponding temporal changes of the voltages of the electrodes (lower curves), when charge sharing occurs and detected voltages are added numerically, according to an embodiment. In this disclosure, numerical addition may be addition of numerical signals of the voltages (i.e., after the voltages are converted to digital signals).

FIG. 6 schematically shows temporal changes of the electric currents flowing through two neighboring electrodes (upper curves) of the X-ray absorption layer exposed to X-ray, the electric currents caused by charge carriers generated by an X-ray photon incident on the X-ray absorption layer, and corresponding temporal changes of the voltages of the electrodes (lower curves), when charge sharing occurs and detected voltages are added numerically, according to an embodiment. The two electrodes may be diodes 310 and 320 shown in FIG. 3A and FIG. 3B, when charge sharing occurs on the two pixels.

The voltage of each electrode may be an integral of the corresponding electric current with respect to time. As discussed above, the two pixels (Pixel 1 and Pixel 2) are in phase 1 when they are ready to detect an X-ray photon. During phase 1, at time $t_0$, the X-ray photon hits at an area near a boundary of or between two neighboring pixels including the two diodes 310 and 320 or two resistors, charge carriers start being generated in the diodes or the resistors, electric current starts to flow through the electrodes of the diodes or the resistors, and the absolute value of each of the two voltages of the electrodes or electrical contacts starts to increase. Then, the two pixels determine that charge sharing occurs at the two pixels.

According to an embodiment, the absolute values of the two voltages start to increase at two different times, e.g. $t_{01}$ and $t_{02}$, that are within a same time period. For example, the same time period may be 10 μs, 1 μs, 100 ns, or 10 ns. If so, the two pixels determine that charge sharing occurs at the two pixels.

As shown in FIG. 6, the two pixels may have different increasing rates of the voltages and/or currents, because the amount of charge carriers transporting into the two pixels may be different. Accordingly, during phase 1, the two voltages may reach the first threshold V1 at different times.

As discussed above, if charge sharing occurs at two pixels, the sum of the voltages measured on these pixels after the voltages are stable may be used to derive the energy of the X-ray photon.

Phase 1 may end at or after the stabilization of the voltages at the two pixels. In the example of FIG. 6, at time $t_e$, all charge carriers generated by the X-ray photon drift out of the X-ray absorption layer 110. As such, the rate of change of the voltage at each pixel may be substantially zero after $t_e$. Here, at time $t_h$ after $t_e$, phase 1 ends.

In this example, the voltage detected at Pixel 2 is numerically added to the voltage detected at Pixel 1, e.g. via a central controller or a bus line. The central controller or a bus line may operate independently from the switches 318, 328, 340. As such, phase 2 may be a very short time period or a time period that can overlap with phase 3 and/or phase 1 after voltage stabilization. If during phase 2, the second voltage comparator 332 of Pixel 1 determines that the absolute value of the added voltage equals or exceeds the absolute value of the second threshold, the controller 336 of Pixel 1 causes the number registered by the counter 338 of Pixel 1 to increase by one.

After the added voltage is obtained, the two pixels may end phase 2 and enter phase 3. In an embodiment, the two pixels may enter phase 3 directly after phase 1, where phase 2 includes numerical voltage adding performed therein and has overlap with the phase 3 and/or phase 1 after voltage stabilization.

During phase 3, each controller 336 connects the electrode to an electric ground for a reset period RST to allow charge carriers accumulated on the electrode to flow to the ground and reset the voltage.

After RST, each system 121 enters phase 1 again and is ready to detect another incident X-ray photon. If the first voltage comparator 331 has been deactivated, the controller 336 can activate it at any time before RST expires. If the controller 336 has been deactivated, it may be activated before RST expires.

FIG. 7 schematically shows temporal changes of the electric currents flowing through the two neighboring electrodes (upper curves) caused by noise (e.g., dark current), and corresponding temporal changes of the voltages of the electrodes (lower curves), in the electronic system operating in the way shown in FIG. 6, according to an embodiment.

In this example, during phase 1, noises begin at the two neighboring pixels (Pixel 1 and Pixel 2) at the same time $t_0$, or within a same time period. Thus, the two pixels cooperate as in the process of FIG. 6.

As discussed above, phase 1 may end at or after the stabilization of the voltages at the two pixels. In the example of FIG. 7, at time $t_e$, the noises end. As such, the rate of change of the voltage at each pixel may be substantially zero after $t_e$. Here, at time $t_h$ after $t_e$, phase 1 ends.

In this example, the voltage detected at Pixel 2 is numerically added to the voltage detected at Pixel 1, e.g. via a central controller or a bus line. The central controller or a bus line may operate independently from the switches 318, 328, 340. As such, phase 2 may be a very short time period or a time period that can overlap with phase 3 and/or phase 1 after voltage stabilization. The noise is very unlikely large enough to cause the absolute value of the added voltage to exceed the absolute value of V2, where the probability of having two noises simultaneously at two neighboring pixel is already very low. Therefore, the controller 336 of Pixel 1 does not cause the number registered by the counter 338 of Pixel 1 to increase. Each controller 336 may be configured not to cause the voltmeter 334 to measure the voltage if the absolute value of the voltage (or added voltage) does not exceed the absolute value of V2 during phase 2.

After the added voltage is obtained, the two pixels may end phase 2 and enter phase 3. In an embodiment, the two pixels may enter phase 3 directly after phase 1, where phase 2 includes numerical voltage adding performed therein and has overlap with the phase 3 and/or phase 1 after voltage stabilization.

During phase 3, each controller 336 connects the electrode to an electric ground for a reset period RST to allow charge carriers accumulated on the electrode as a result of the noise to flow to the ground and reset the voltage. Therefore, the electronic systems 121 may be very effective in noise rejection, even if voltage adding is activated for potential charge sharing management and performed numerically.

Figure 8A:
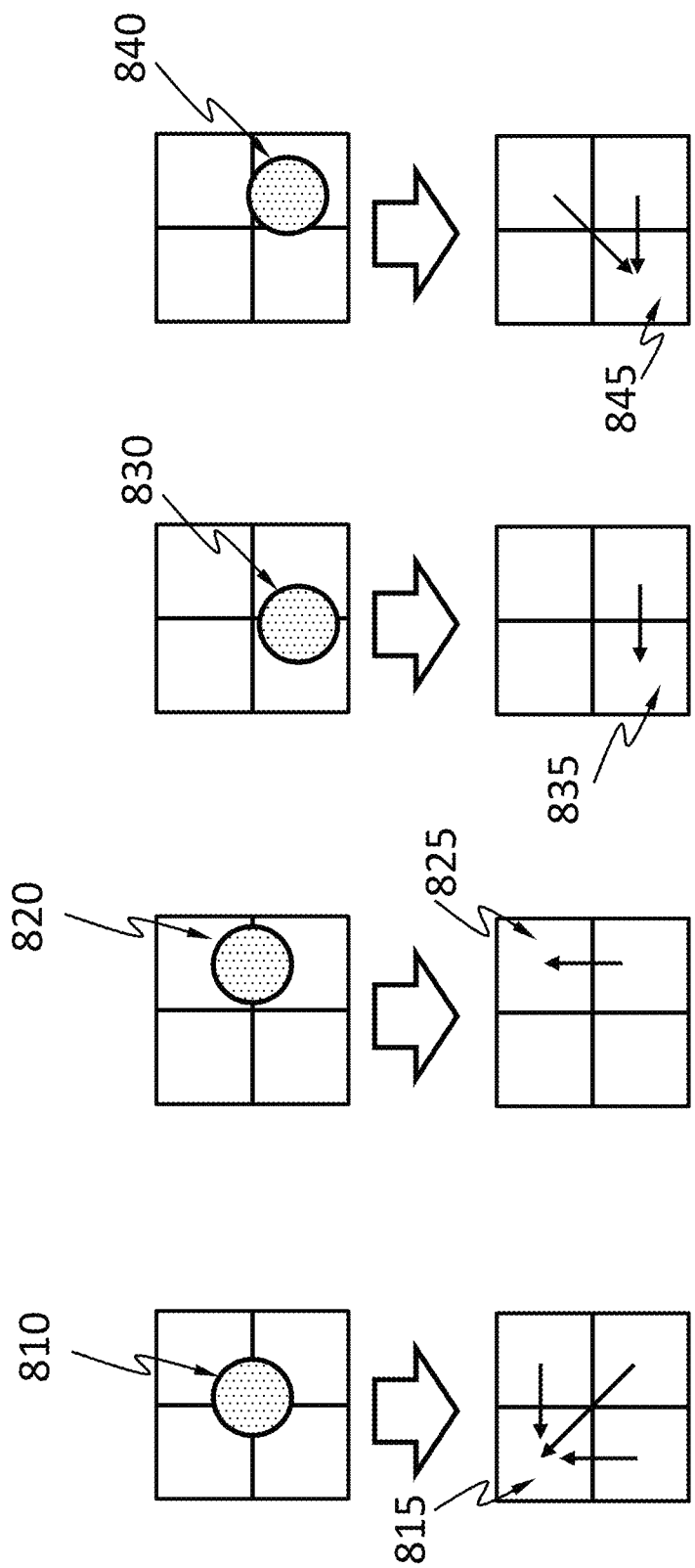
FIG. 8A illustrates various examples of assigning an X-ray photon causing charge sharing at multiple pixels to one of the pixels to form an image, according to an embodiment.

FIG. 8A illustrates various examples of assigning or measuring the energy of an X-ray photon causing charge sharing at multiple pixels to one of the pixels to, according to an embodiment. As discussed above, when charge sharing caused by an X-ray photon occurs at two or more neighboring pixels, the voltage adding may be performed at a chosen pixel of the neighboring pixels, and the X-ray photon may be assigned to or whose energy measured by the chosen pixel. In one embodiment, the X-ray photon may be assigned to a pixel, based on a strategy different from the strategy used for choosing the pixel to perform voltage adding. For non-imaging applications, it does not matter which pixel the photon is assigned to.

FIG. 8A illustrates a strategy to choose one of neighboring pixels, either for performing voltage adding or for assigning the X-ray photon. As shown in FIG. 8A, when the transport area 810 sits across four neighboring pixels, the upper left pixel 815 is chosen. When the transport area 820 sits on a boundary of two neighboring pixels that are vertically adjacent, the upper pixel 825 is chosen. When the transport area 830 sits on a boundary of two neighboring pixels that are horizontally adjacent, the left pixel 835 is chosen. When the transport area 840 sits across three pixels (lower left, lower right, and upper right) as shown in FIG. 8A, the lower left pixel 845 is chosen. As such, the strategy shown in FIG. 8A prefers a left pixel to a right pixel, prefers an upper pixel to a lower pixel, and prefer a lower left pixel to an upper right pixel. According to an embodiment, a different strategy to choose one of neighboring pixels may be based on a different preference of relative positions of the neighboring pixels. According to another embodiment, a different strategy to choose one of neighboring pixels may be based on a comparison of the absolute value of the voltages detected at the neighboring pixels, after stabilization of voltage on these pixels. For example, the pixel having a highest absolute value of detected voltage of electrode may be chosen.

Figure 8B:
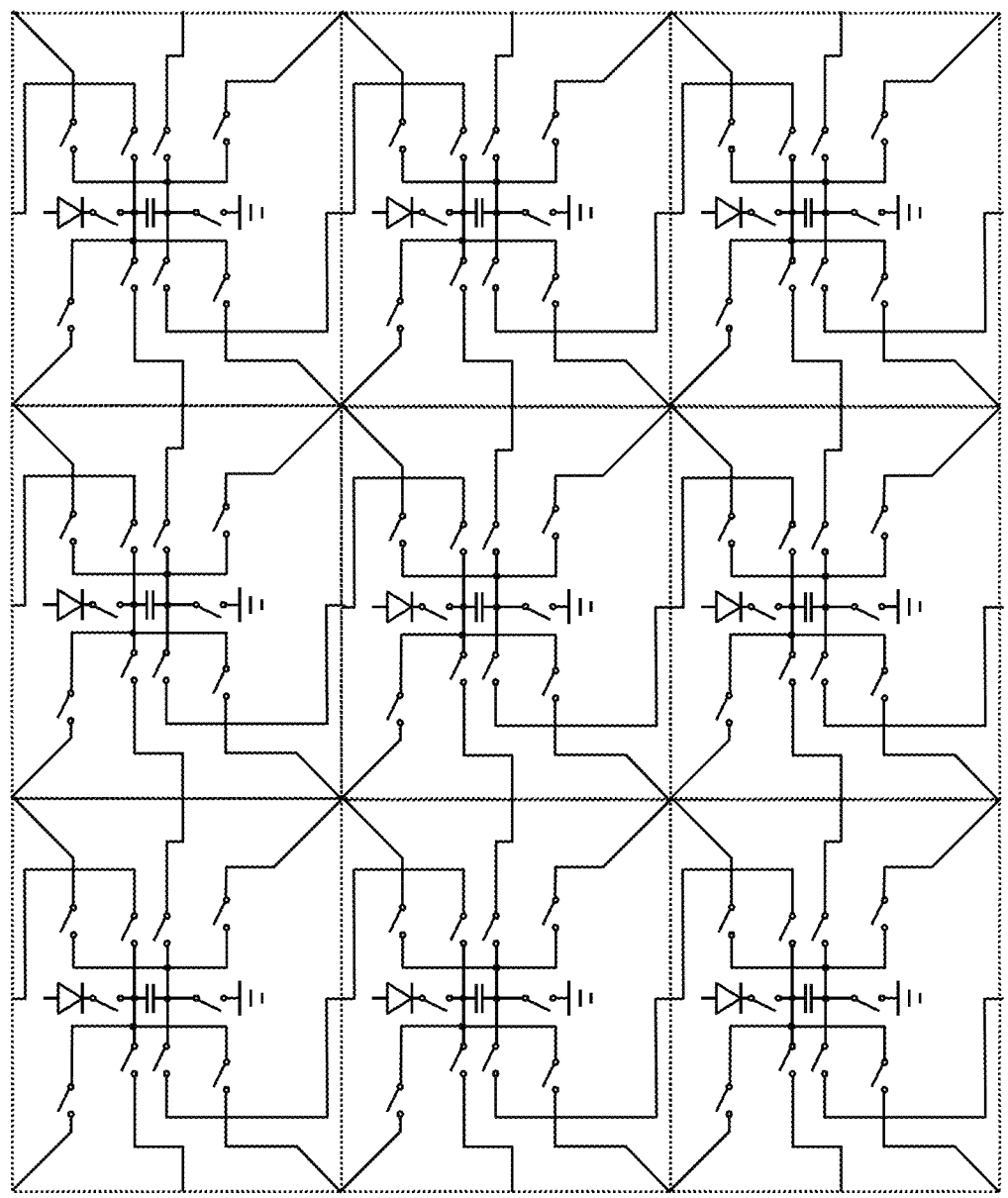
FIG. 8B shows an example of a circuit that can implement the strategy of FIG. 8A.

FIG. 8B shows an example of a circuit that can implement the strategy of FIG. 8A.

Figure 9A:
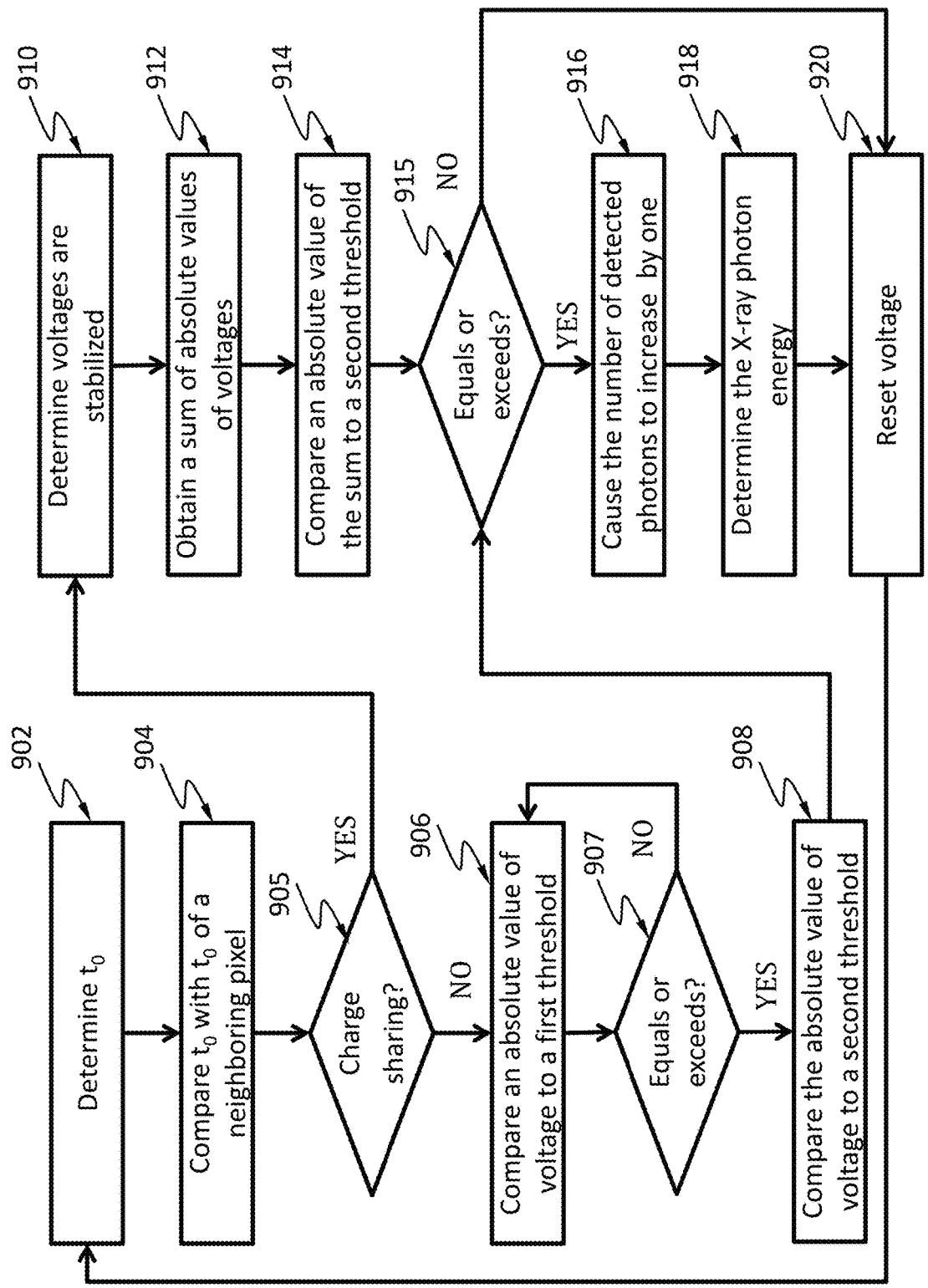
FIG. 9A shows a flow chart for a method suitable for detecting X-ray based on a system such as the electronic system 121 of Pixel 1 in FIG. 3A and FIG. 3B, according to an embodiment.

FIG. 9A shows a flow chart for a method suitable for detecting X-ray based on a system such as the electronic system 121 of Pixel 1 in FIG. 3A and FIG. 3B, according to an embodiment. At 902, determine a time $t_0$ at which a voltage of an electrode starts to increase. The electrode may be a diode or an electrical contact of a resistor exposed to X-ray. At 904, compare the time $t_0$ with that of a neighboring pixel. At 905, it is determined whether charge sharing occurs, e.g. by determining whether the time $t_0$ of the Pixel 1 and the time $t_0$ of a neighboring pixel are within a same time period, e.g. 10 µs, 1 µs, 100 ns, or 10 ns. If charge sharing occurs, the process moves to 910. Otherwise, if charge sharing does not occur, the process moves to 906.

At 906, compare, e.g., using the first voltage comparator 331, an absolute value of the voltage of an electrode of a diode or an electrical contact of a resistor exposed to X-ray, to a first threshold V1. At 907, if the absolute value of the voltage does not equal or exceed the absolute value of the first threshold, the process goes back to step 906. If the absolute value of the voltage equals or exceeds the absolute value of the first threshold at 907, the process continues to step 908, e.g. after a time delay or after the voltage is stabilized. At 908, compare, e.g., using the second voltage comparator 332, the absolute value of the voltage to a second threshold. Then, the process moves to 913.

At 910, determine voltages are stabilized at Pixel 1 and the neighboring pixel(s), e.g. by determining that the rate of change of the voltage at each pixel is substantially zero for a time period, e.g. 1 ms or 0.1 ms. At 912, obtain a sum of absolute values of voltages of Pixel 1 and the neighboring pixel(s). At 914, compare, e.g., using the second voltage comparator 332, an absolute value of the sum voltage to a second threshold. Then, the process moves to 915.

At 915, if the absolute value of the voltage or the sum voltage does not equal or exceed the absolute value of the second threshold, the process goes to step 920. If the absolute value of the voltage or the sum voltage equals or exceeds the absolute value of the second threshold, the process continues to step 916. At 916, cause, e.g., using the controller 336, the number registered in the counter 338 to increase by one. At 918, determine, e.g., using the controller 336, the X-ray photon energy based on the voltage or the sum voltage. There may be a counter for each of the energy bins. After measuring the X-ray photon energy, the counter for the bin to which the photon energy belongs can be increased by one. The method goes to step 920 after step 918. At 920, reset the voltage to an electrical ground, e.g., by connecting the electrode of the diode or an electrical contact of a resistor to an electrical ground. After 920, the process may go back to 902.

Figure 9B:
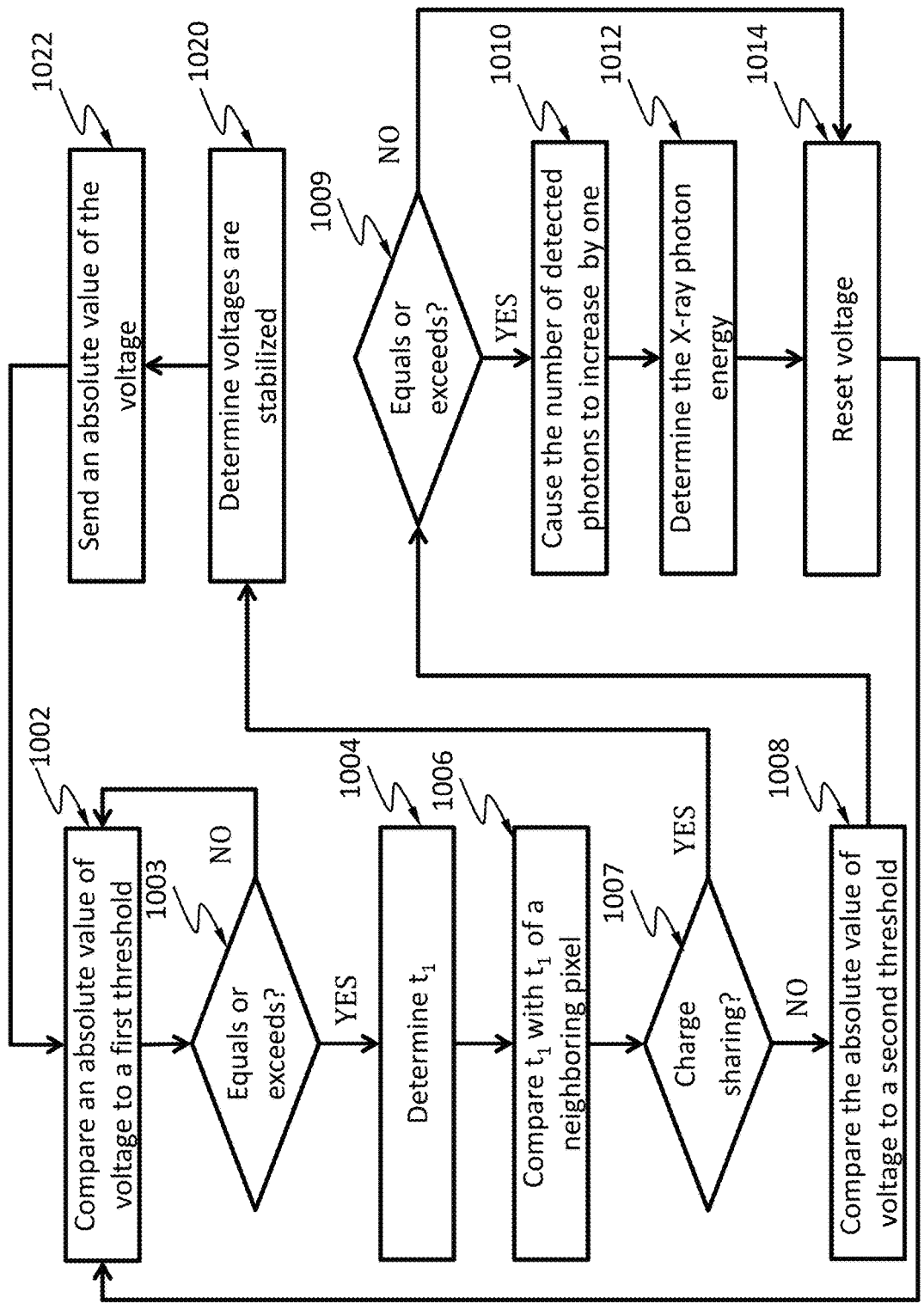
FIG. 9B shows a flow chart for a method suitable for detecting X-ray based on a system such as the electronic system 121 of Pixel 2 in FIG. 3A and FIG. 3B, according to an embodiment.

FIG. 9B shows a flow chart for a method suitable for helping to detect X-ray based on a system such as the electronic system 121 of Pixel 2 in FIG. 3A and FIG. 3B, according to an embodiment. At 1002, compare, e.g., using the first voltage comparator 331, an absolute value of the voltage of an electrode of a diode or an electrical contact of a resistor exposed to X-ray, to a first threshold V1. At 1003, if the absolute value of the voltage does not equal or exceed the absolute value of the first threshold, the process goes back to step 1002. If the absolute value of the voltage equals or exceeds the absolute value of the first threshold at 1003, the process continues to step 1004.

At 1004, determine a time $t_1$ at which the voltage of the electrode reaches first threshold V1. At 1006, compare the time $t_1$ with that of a neighboring pixel. At 1007, it is determined whether charge sharing occurs, e.g. by determining whether the time $t_1$ of the Pixel 2 and the time $t_1$ of a neighboring pixel are within a same time period, e.g. 10 μs, 1 μs, 100 ns, or 10 ns. If charge sharing occurs, the process moves to 1020. At 1020, determine voltages are stabilized at Pixel 2 and the neighboring pixel, e.g. by determining that the rate of change of the voltage at each pixel is substantially zero for a time period, e.g. 1 ms or 0.1 ms. At 1022, the absolute value of the voltage of Pixel 2 is sent to the neighboring pixel for voltage adding, either by capacitor serial connection or by numerical adding. After 1022, the process may go back to 1002.

Otherwise, if charge sharing does not occur at 1007, the process moves to 1008, e.g. after a time delay or after the voltage is stabilized. At 1008, compare, e.g., using the second voltage comparator 332, the absolute value of the voltage to a second threshold. At 1009, if the absolute value of the voltage does not equal or exceed the absolute value of the second threshold, the process goes to step 1014. If the absolute value of the voltage equals or exceeds the absolute value of the second threshold at 1009, the process continues to step 1010. At 1010, cause, e.g., using the controller 336, the number registered in the counter 338 to increase by one. At 1012, determine, e.g., using the controller 336, the X-ray photon energy based on the voltage. There may be a counter for each of the energy bins. After measuring the X-ray photon energy, the counter for the bin to which the photon energy belongs can be increased by one. The method goes to step 1014 after step 1012. At 1014, reset the voltage to an electrical ground, e.g., by connecting the electrode of the diode or an electrical contact of a resistor to an electrical ground. After 1014, the process may go back to 1002.

Figure 9C:
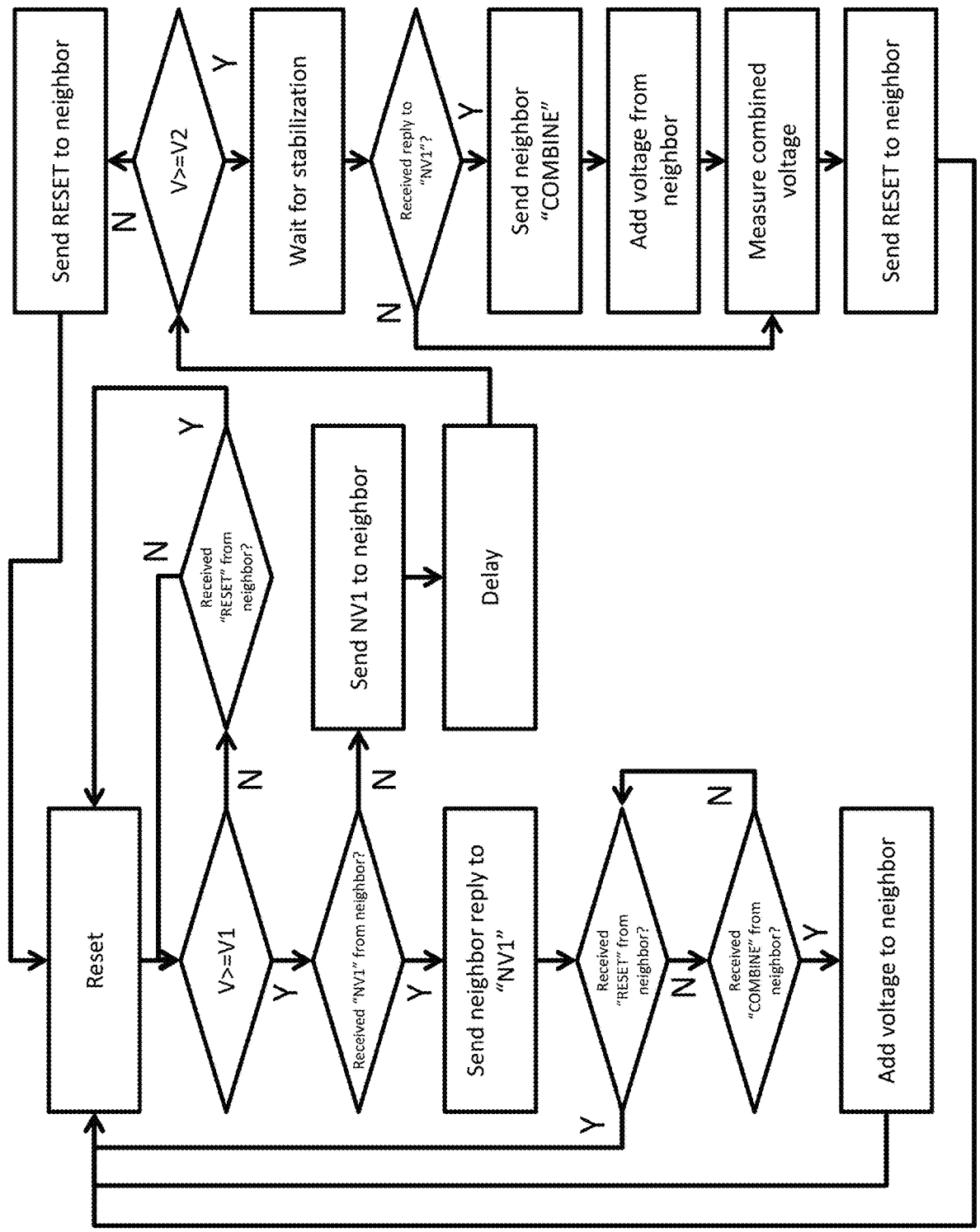
FIG. 9C shows a flow chart for a method of determining occurrence of charge sharing and combining voltages generated on neighboring pixels by a shared X-ray photon, according to an embodiment.

FIG. 9C shows a flow chart for a method of determining occurrence of charge sharing and combining voltages generated on neighboring pixels by a shared X-ray photon, according to an embodiment. In this flow chart, there are several signals passed between neighboring pixels. The signal "RESET" tells the pixel receiving it to reset its voltage and any stored signal. The signal "NV1" a pixel sends to a neighboring pixel tells the neighboring pixel that the voltage on the pixel is V1 or higher. The signal "COMBINE" a pixel sends to a neighboring pixel tells the neighboring pixel to combine its voltage to the voltage of the pixel.

The semiconductor X-ray detector 100 may be used for phase-contrast X-ray imaging (PCI) (also known as phase-sensitive X-ray imaging). PCI encompasses techniques that form an image of an object at least partially using the phase shift (including the spatial distribution of the phase shift) of an X-ray beam caused by that object. One way to obtain the phase shift is transforming the phase into variations in intensity.

PCI can be combined with tomographic techniques to obtain the 3D-distribution of the real part of the refractive index of the object. PCI is more sensitive to density variations in the object than conventional intensity-based X-ray imaging (e.g., radiography). PCI is especially useful for imaging soft tissues.

According to an embodiment, FIG. 10 schematically shows a system 1900 suitable for PCI. The system 1900 may include at least two X-ray detectors 1910 and 1920. One or both of the two X-ray detectors 1910 is the semiconductor X-ray detector 100 described herein. The X-ray detectors 1910 and 1920 may be spaced apart by a spacer 1930. The spacer 1930 may have very little absorption of the X-ray. For example, the spacer 1930 may have a very small mass attenuation coefficient (e.g., <10 cm$^2$ g$^{-1}$, <1 cm$^2$ g$^{-1}$, <0.1 cm$^2$ g$^{-1}$, or <0.01 cm$^2$ g$^{-1}$). The mass attenuation coefficient of the spacer 1930 may be uniform (e.g., variation between every two points in the spacer 1930 less than 5%, less than 1% or less than 0.1%). The spacer 1930 may cause the same amount of changes to the phase of X-ray passing through the spacer 1930. For example, the spacer 1930 may be a gas (e.g., air), a vacuum chamber, may comprise aluminum, beryllium, silicon, or a combination thereof.

The system 1900 can be used to obtain the phase shift of incident X-ray 1950 caused by an object 1960 being imaged. The X-ray detectors 1910 and 1920 can capture two images (i.e., intensity distributions) simultaneously. Because of the X-ray detectors 1910 and 1920 are separated by the spacer 1930, the two images are different distances from the object 1960. The phase may be determined from the two images, for example, using algorithms based on the linearization of the Fresnel diffraction integral.

According to an embodiment, FIG. 11 schematically shows a system 1800 suitable for PCI. The system 1800 comprises the semiconductor X-ray detector 100 described herein. The semiconductor X-ray detector 100 is configured to move to and capture images of an object 1860 exposed to incident X-ray 1850 at different distances from the object 1860. The images may not necessarily be captured simultaneously. The phase may be determined from the images, for example, using algorithms based on the linearization of the Fresnel diffraction integral.

Figure 12:
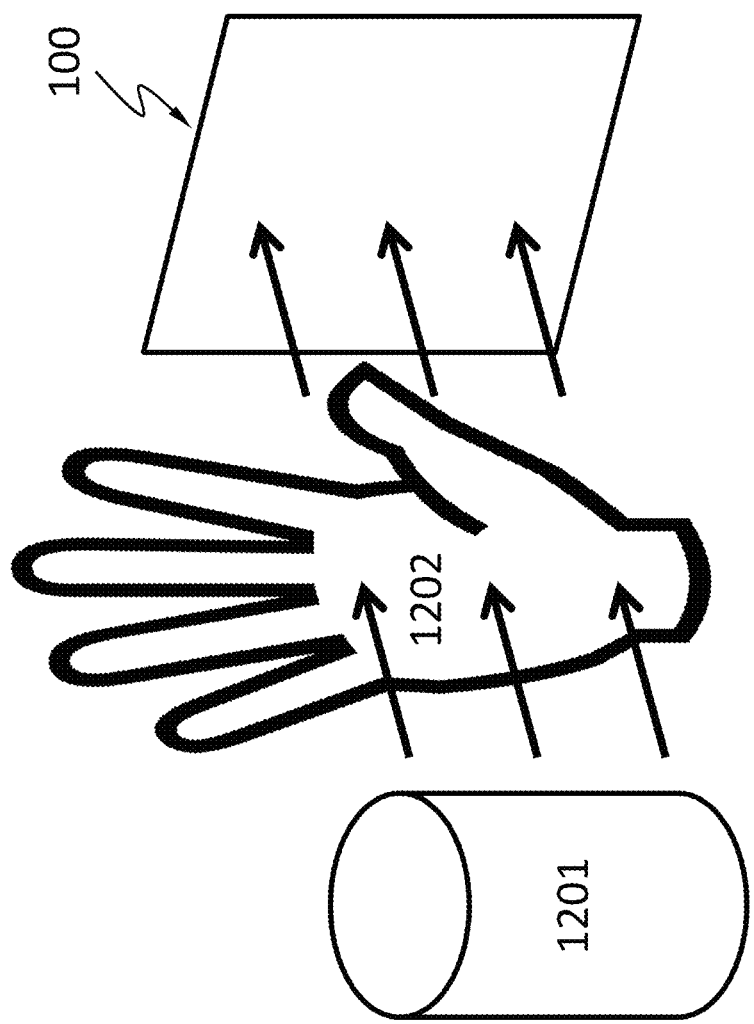
FIG. 12 schematically shows a system comprising the semiconductor X-ray detector described herein, suitable for medical imaging such as chest X-ray radiography, abdominal X-ray radiography, etc., according to an embodiment.

FIG. 12 schematically shows a system comprising the semiconductor X-ray detector 100 described herein. The system may be used for medical imaging such as chest X-ray radiography, abdominal X-ray radiography, etc. The system comprises an X-ray source 1201. X-ray emitted from the X-ray source 1201 penetrates an object 1202 (e.g., a human body part such as chest, limb, abdomen), is attenuated by different degrees by the internal structures of the object 1202 (e.g., bones, muscle, fat and organs, etc.), and is projected to the semiconductor X-ray detector 100. The semiconductor X-ray detector 100 forms an image by detecting the intensity distribution of the X-ray.

Figure 13:
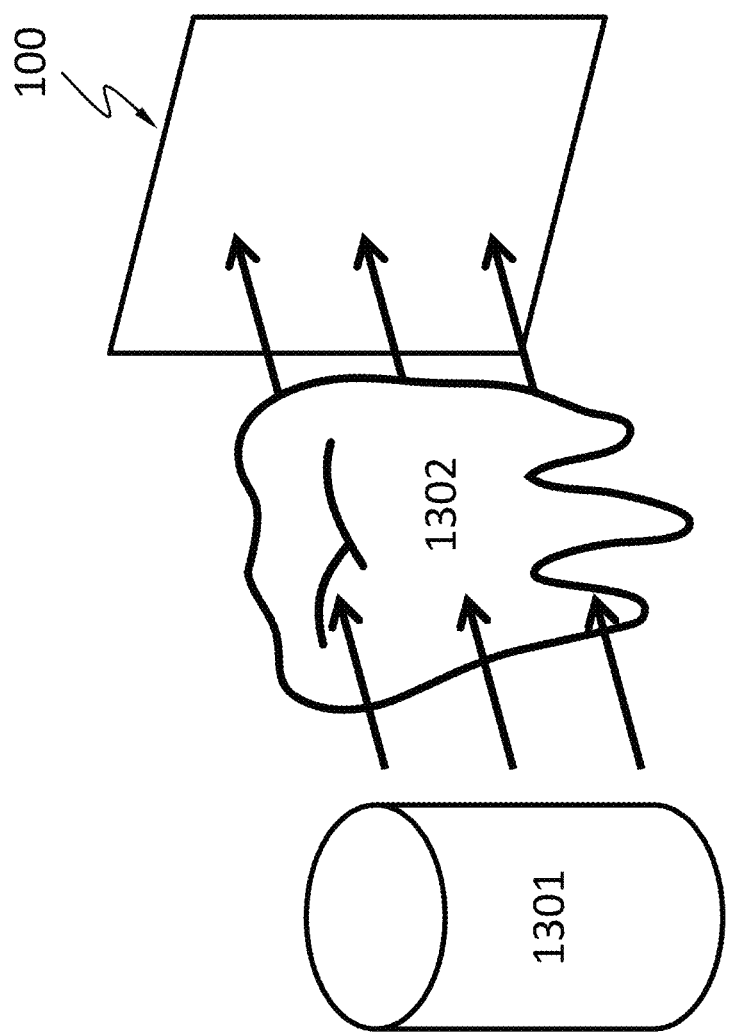
FIG. 13 schematically shows a system comprising the semiconductor X-ray detector described herein suitable for dental X-ray radiography, according to an embodiment.

FIG. 13 schematically shows a system comprising the semiconductor X-ray detector 100 described herein. The system may be used for medical imaging such as dental X-ray radiography. The system comprises an X-ray source 1301. X-ray emitted from the X-ray source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the semiconductor X-ray detector 100. The semiconductor X-ray detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 14:
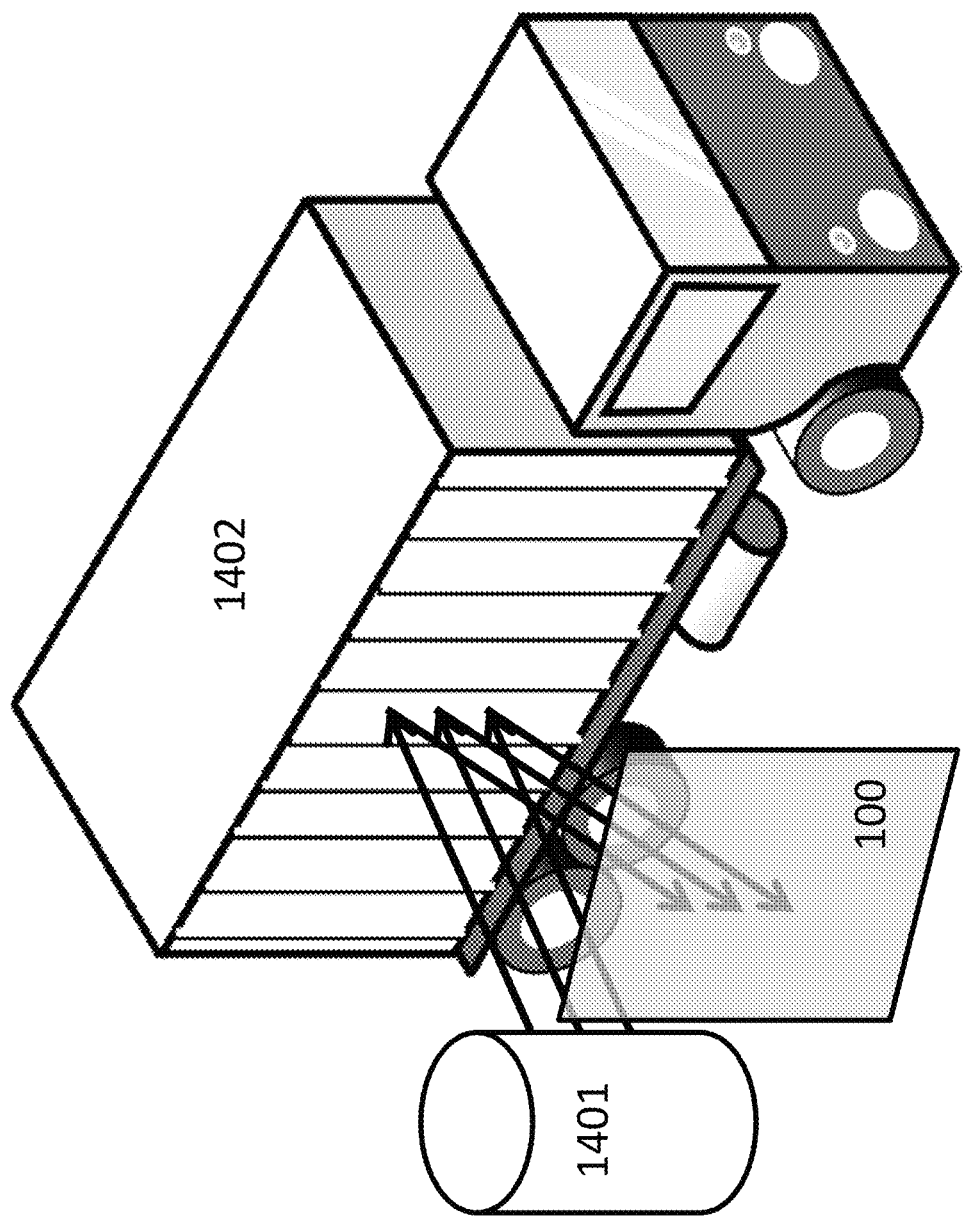
FIG. 14 schematically shows a cargo scanning or non-intrusive inspection (NII) system comprising the semiconductor X-ray detector described herein, according to an embodiment.

FIG. 14 schematically shows a cargo scanning or non-intrusive inspection (NII) system comprising the semiconductor X-ray detector 100 described herein. The system may be used for inspecting and identifying goods in transportation systems such as shipping containers, vehicles, ships, luggage, etc. The system comprises an X-ray source 1401. X-ray emitted from the X-ray source 1401 may backscatter from an object 1402 (e.g., shipping containers, vehicles, ships, etc.) and be projected to the semiconductor X-ray detector 100. Different internal structures of the object 1402 may backscatter X-ray differently. The semiconductor X-ray detector 100 forms an image by detecting the intensity distribution of the backscattered X-ray and/or energies of the backscattered X-ray photons.

Figure 15:
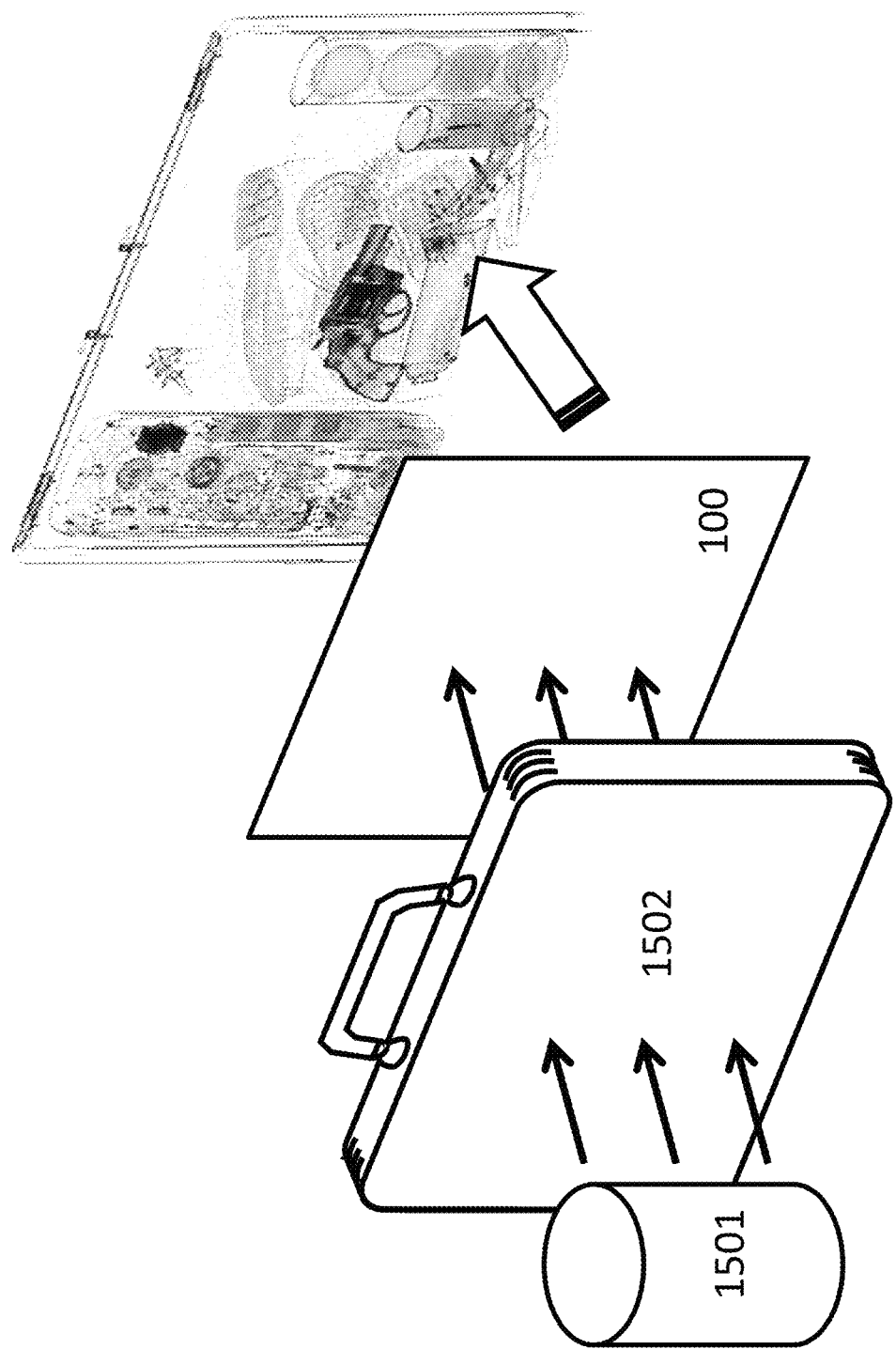
FIG. 15 schematically shows another cargo scanning or non-intrusive inspection (NII) system comprising the semiconductor X-ray detector described herein, according to an embodiment.

FIG. 15 schematically shows another cargo scanning or non-intrusive inspection (NII) system comprising the semiconductor X-ray detector 100 described herein. The system may be used for luggage screening at public transportation stations and airports. The system comprises an X-ray source 1501. X-ray emitted from the X-ray source 1501 may penetrate a piece of luggage 1502, be differently attenuated by the contents of the luggage, and projected to the semiconductor X-ray detector 100. The semiconductor X-ray detector 100 forms an image by detecting the intensity distribution of the transmitted X-ray. The system may reveal contents of luggage and identify items forbidden on public transportation, such as firearms, narcotics, edged weapons, flammables.

Figure 16:
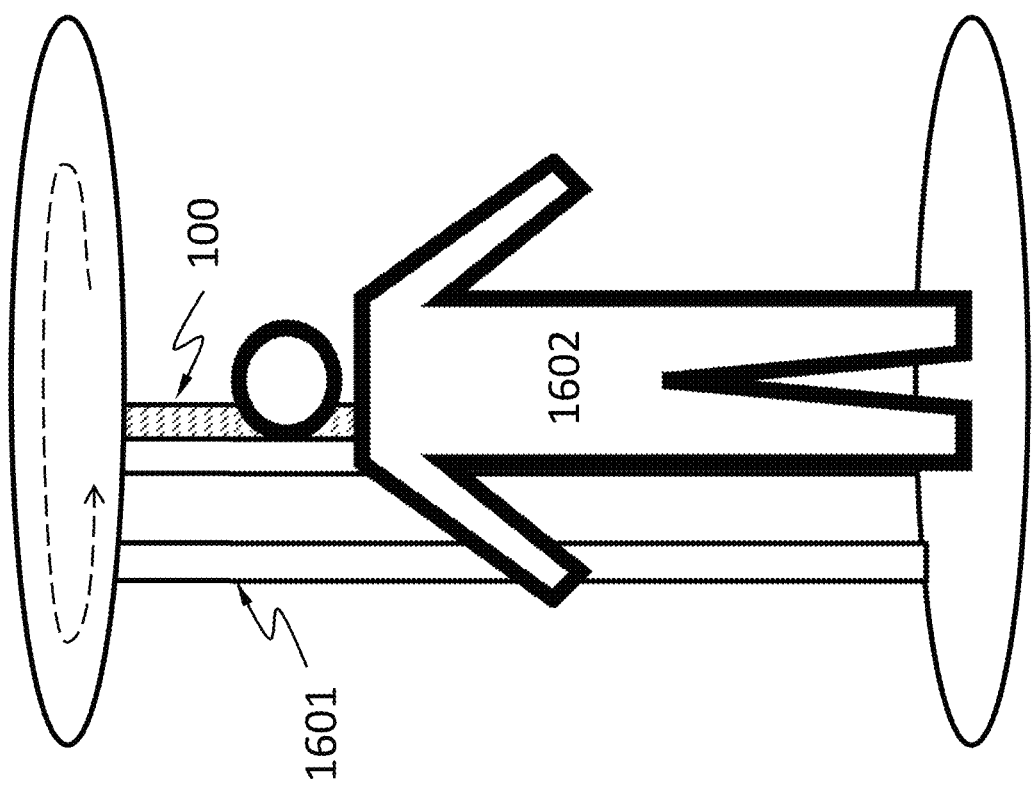
FIG. 16 schematically shows a full-body scanner system comprising the semiconductor X-ray detector described herein, according to an embodiment.

FIG. 16 schematically shows a full-body scanner system comprising the semiconductor X-ray detector 100 described herein. The full-body scanner system may detect objects on a person's body for security screening purposes, without physically removing clothes or making physical contact. The full-body scanner system may be able to detect non-metal objects. The full-body scanner system comprises an X-ray source 1601. X-ray emitted from the X-ray source 1601 may backscatter from a human 1602 being screened and objects thereon, and be projected to the semiconductor X-ray detector 100. The objects and the human body may backscatter X-ray differently. The semiconductor X-ray detector 100 forms an image by detecting the intensity distribution of the backscattered X-ray. The semiconductor X-ray detector 100 and the X-ray source 1601 may be configured to scan the human in a linear or rotational direction.

Figure 17:
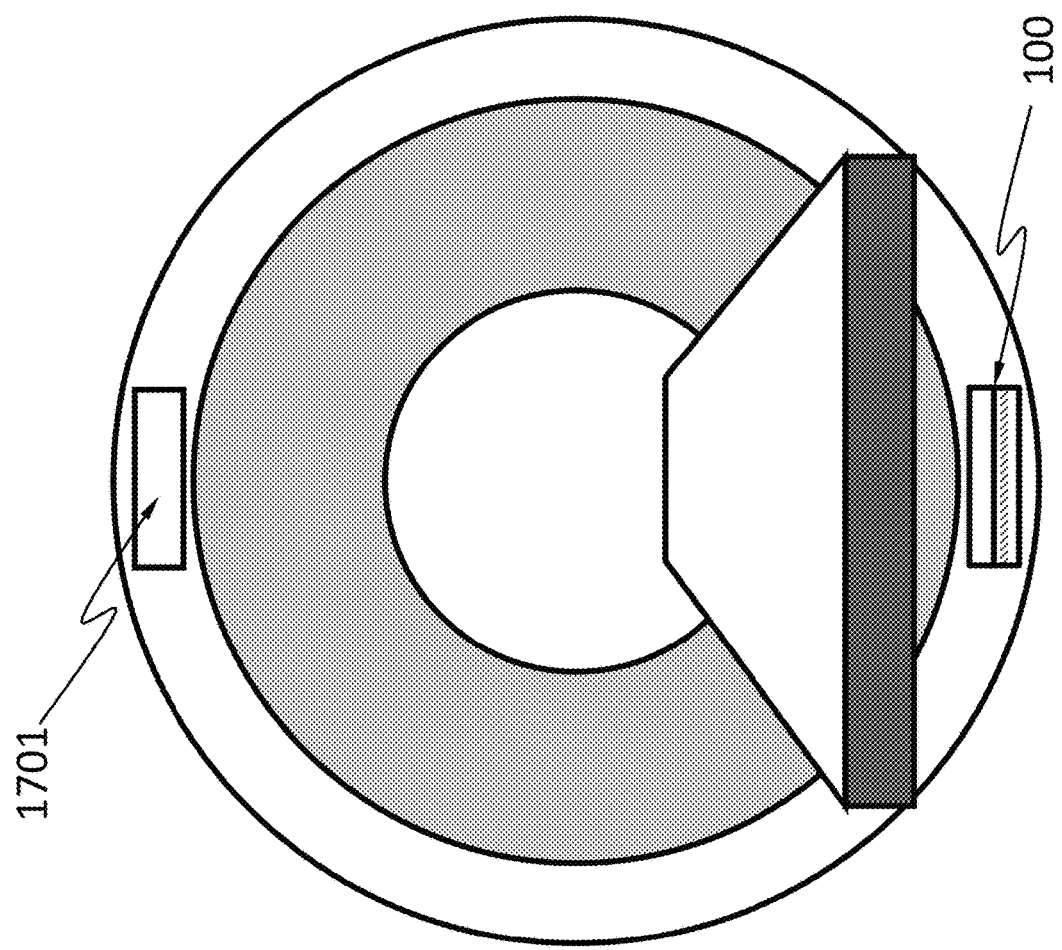
FIG. 17 schematically shows an X-ray computed tomography (X-ray CT) system comprising a semiconductor X-ray detector described herein, according to an embodiment.

FIG. 17 schematically shows an X-ray computed tomography (X-ray CT) system comprising the semiconductor X-ray detector 100 described herein. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the semiconductor X-ray detector 100 described herein and an X-ray source 1701. The semiconductor X-ray detector 100 and the X-ray source 1701 may be configured to rotate synchronously along one or more circular or spiral paths.

Figure 18:
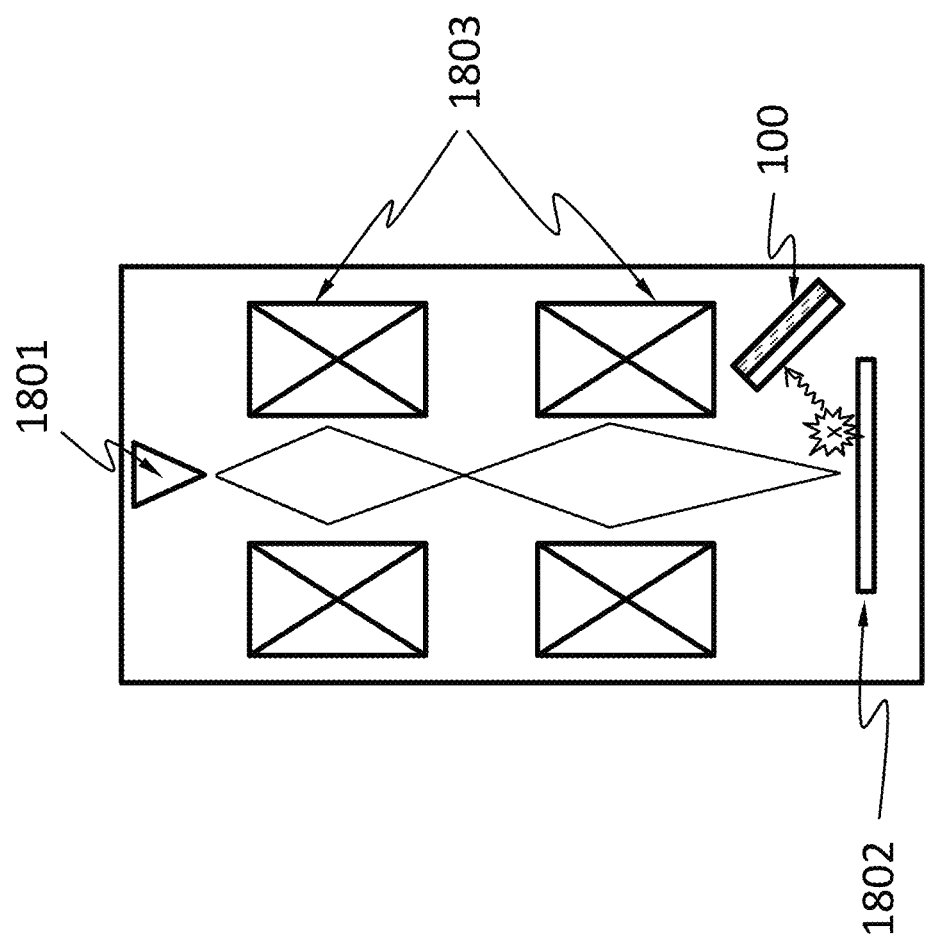
FIG. 18 schematically shows an electron microscope comprising the semiconductor X-ray detector described herein, according to an embodiment.

FIG. 18 schematically shows an electron microscope comprising the semiconductor X-ray detector 100 described herein. The electron microscope comprises an electron source 1801 (also called an electron gun) that is configured to emit electrons. The electron source 1801 may have various emission mechanisms such as thermionic, photo-cathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the semiconductor X-ray detector 100 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the semiconductor X-ray detector 100.

Figure 19:
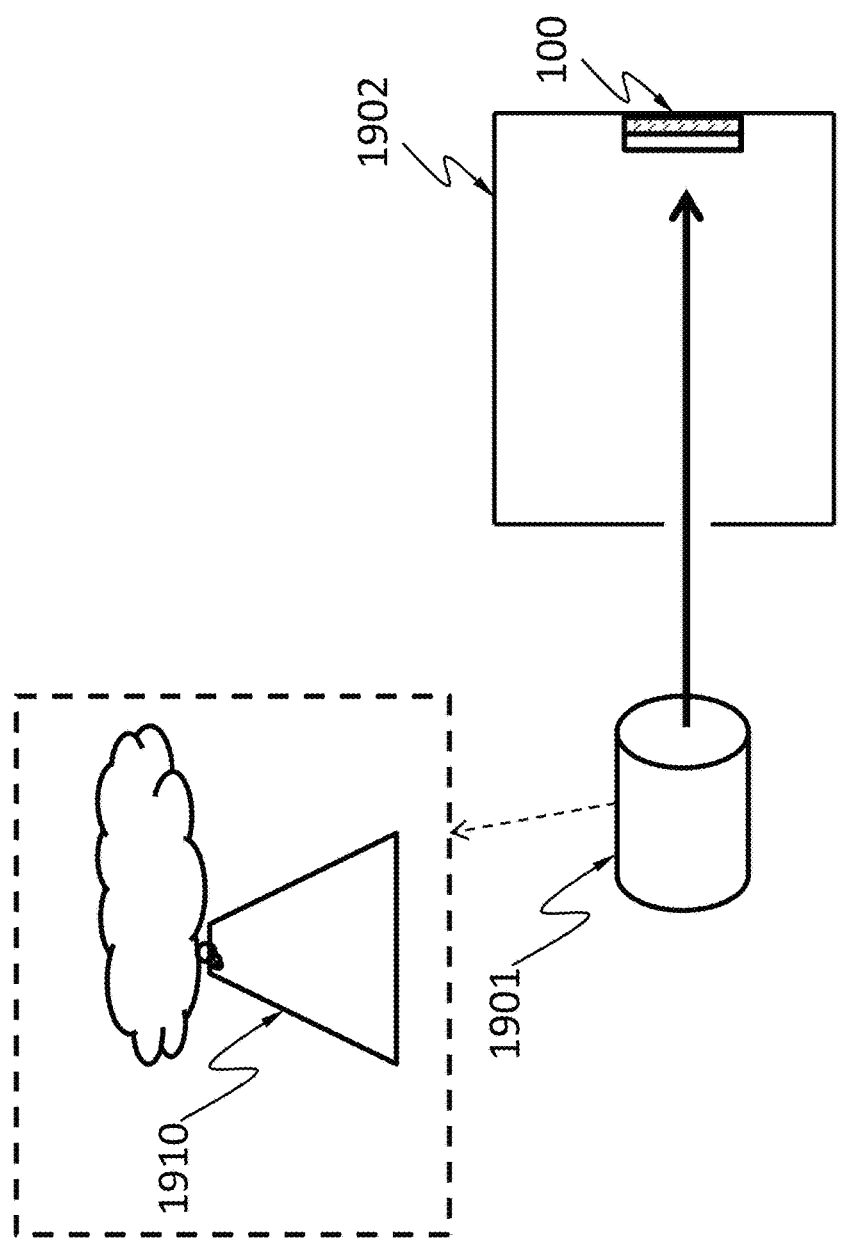
FIG. 19 schematically shows a radiation dose meter, according to an embodiment.

FIG. 19 schematically shows a radiation dose meter comprising the semiconductor X-ray detector 100 described herein. The radiation dose meter is capable of measuring an average dose rate of a radiation, e.g. X-ray, from a radiation source 1901. The radiation source 1901 may be a volcano 1910 or an atom bomb explosion. The radiation dose meter may include a chamber 1902 that includes air or other gas.

X-ray going through a gas will ionize it, producing positive ions and free electrons. An incoming photon will create a number of such ion pairs proportional to its energy. An X-ray detector associated with the radiation dose meter can measure the average dose rate over the gas volume or the number of interacting photons. While the X-ray detector in the non-image application is usually a single pixel detector, the X-ray detector 100 having a plurality of pixels described herein can also be utilized with the capability of managing charge sharing that may occur on neighboring pixels.

Figure 20:
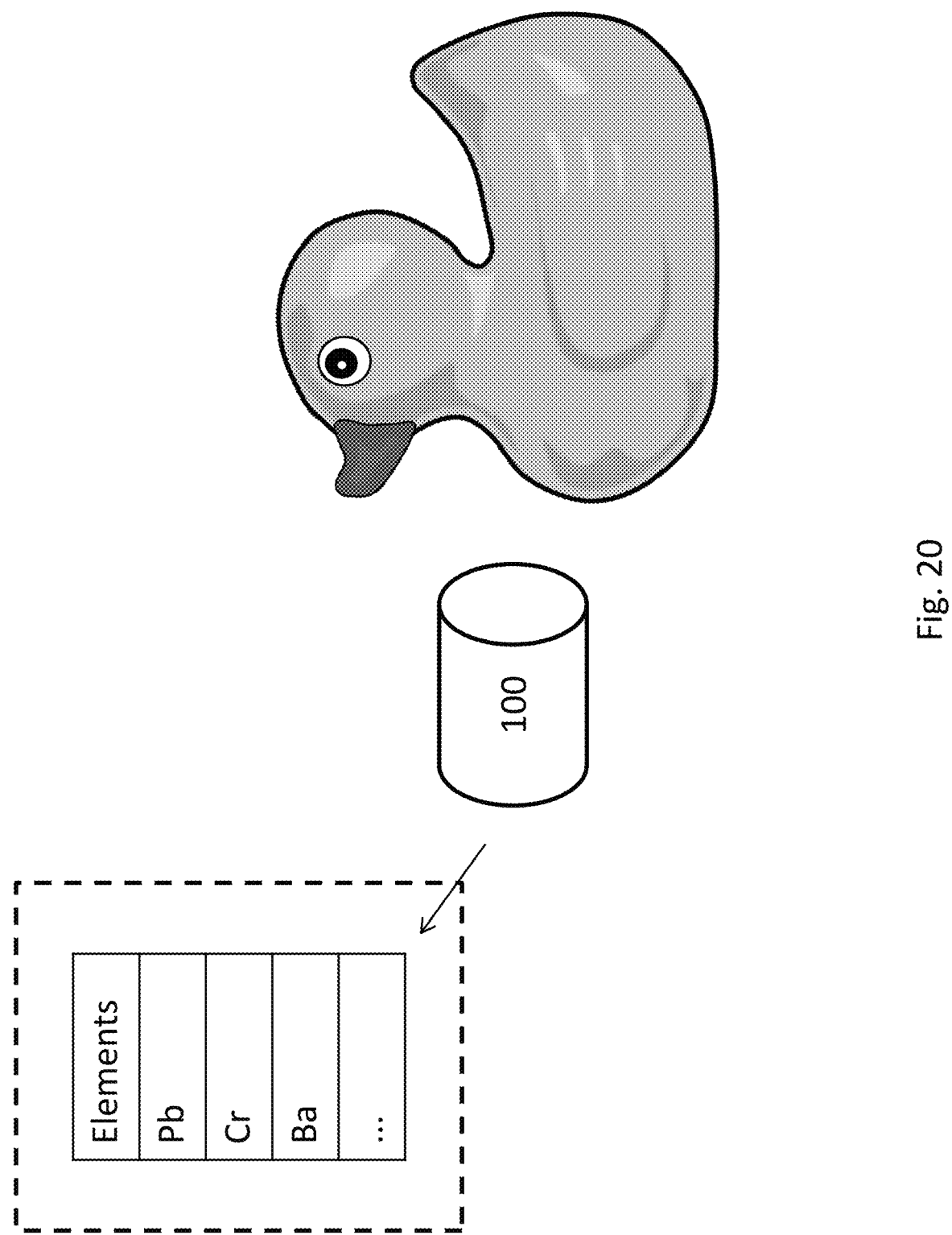
FIG. 20 schematically shows an element analyzer, according to an embodiment.

FIG. 20 schematically shows an element analyzer comprising the semiconductor X-ray detector 100 described herein. The element analyzer measurer is capable of detecting presence of one or more elements of interest on an object such as a toy. A high-energy beam of charged particles such as electrons or protons, or a beam of X-rays, is directed onto the object. Atoms of the objects are excited and emit X-ray at specific wavelengths that are characteristic of the elements. The X-ray detector 100 receives the emitted X-ray and determines the presence of the elements based on the energy of the emitted X-ray. For example, the X-ray detector 100 may be configured to detect X-ray at wavelengths Pb would emit. If the X-ray detector 100 actually receives X-ray from the object at these wavelengths, it can tell that Pb is present. The semiconductor X-ray detector 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this semiconductor X-ray detector 100 in place of a photographic plate, a photographic film, a PSP plate, an X-ray image intensifier, a scintillator, or another semiconductor X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus suitable for detecting X-ray, comprising:
   an X-ray absorption layer comprising a first pixel and a second pixel; and
   a controller configured for:
     determining that carriers generated by a single X-ray photon are collected by the first pixel and the second pixel,
     determining energy of the single X-ray photon based on a first voltage detected from the first pixel and a second voltage detected from the second pixel, wherein the first voltage and the second voltage are caused by the single X-ray photon,
     obtaining a sum of an absolute value of the first voltage and an absolute value of the second voltage, and
     determining the energy of the single X-ray photon based on the sum wherein:
   the first pixel is associated with a first capacitor charged with the first voltage;
   the second pixel is associated with a second capacitor charged with the second voltage; and
   the sum is obtained by serially connecting the first capacitor and the second capacitor and measuring a voltage across the serially connected capacitors.

2. The apparatus of claim 1, wherein the sum is obtained by numerically adding the absolute value of the first voltage and the absolute value of the second voltage.

3. The apparatus of claim 1, further comprising a counter configured for registering a number of X-ray photons absorbed by the X-ray absorption layer, wherein the controller is configured for causing the number registered by the counter to increase by one, when the sum equals or exceeds a predetermined threshold.

4. The apparatus of claim 1, wherein the energy of the single X-ray photon is determined when a rate of change of the first voltage and a rate of change of the second voltage are substantially zero.

5. The apparatus of claim 1, wherein the controller is configured for determining that carriers generated by a single X-ray photon are collected by the first pixel and the second pixel, when the first voltage and the second voltage start to change in a same time period.

6. The apparatus of claim 1, wherein the controller is configured for determining that carriers generated by a single X-ray photon are collected by the first pixel and the second pixel, when an absolute value of the first voltage and an absolute value of the second voltage reach a first threshold in a same time period.

7. The apparatus of claim 1, wherein the X-ray photon is assigned to one of the first pixel and the second pixel to form an image, based on at least one of the following:
   a comparison of the first voltage and the second voltage; and
   relative positions of the first pixel and the second pixel.

8. The apparatus of claim 1, wherein the apparatus comprises an array of pixels.

9. A system comprising the apparatus of claim 1 and an X-ray source, wherein the system is configured for performing X-ray radiography on human chest or abdomen.

10. A system comprising the apparatus of claim 1 and an X-ray source, wherein the system is configured for performing X-ray radiography on human mouth.

11. A cargo scanning or non-intrusive inspection (NII) system, comprising the apparatus of claim 1 and an X-ray source, wherein the cargo scanning or non-intrusive inspection (NII) system is configured for forming an image based on backscattered X-ray.

12. A cargo scanning or non-intrusive inspection (NII) system, comprising the apparatus of claim 1 and an X-ray source, wherein the cargo scanning or non-intrusive inspection (NII) system is configured for forming an image based on X-ray transmitted through an object inspected.

13. A full-body scanner system comprising the apparatus of claim 1 and an X-ray source.

14. An X-ray computed tomography (X-ray CT) system comprising the apparatus of claim 1 and an X-ray source.

15. An electron microscope comprising the apparatus of claim 1, an electron source and an electronic optical system.

16. A system comprising the apparatus of claim 1, wherein the system is configured for measuring dose of an X-ray source.

17. A system comprising the apparatus of claim 1, wherein the system is an X-ray telescope, or an X-ray microscopy, or wherein the system is configured for performing mammography, industrial defect detection, microradiography, casting inspection, weld inspection, or digital subtraction angiography.

18. A system suitable for phase-contrast X-ray imaging (PCI), the system comprising the apparatus of claim 1, wherein the apparatus is configured for moving to and capturing images of an object exposed to incident X-ray at different distances from the object.

19. A method comprising:
- determining that carriers generated by a single X-ray photon are collected by a first pixel and a second pixel;
- detecting a first voltage from the first pixel;
- detecting a second voltage from the second pixel;
- determining energy of the single X-ray photon based on the first voltage and the second voltage, wherein the first voltage and the second voltage are caused by the single X-ray photon;
- obtaining a sum of an absolute value of the first voltage and an absolute value of the second voltage; and
- determining the energy of the single X-ray photon based on the sum;
- wherein the first pixel is associated with a first capacitor charged with the first voltage;
- wherein the second pixel is associated with a second capacitor charged with the second voltage; and
- wherein the sum is obtained by serially connecting the first capacitor and the second capacitor and measuring a voltage across the serially connected capacitors.

20. The method of claim 19, wherein the sum is obtained by numerically adding the absolute value of the first voltage and the absolute value of the second voltage.

21. The method of claim 19, further comprising increasing a count of X-ray photon incident on an X-ray absorption layer comprising the first pixel and the second pixel by one, when the sum equals or exceeds a predetermined threshold.

22. The method of claim 19, wherein the energy of the single X-ray photon is determined when a rate of change of the first voltage and a rate of change of the second voltage are substantially zero.

23. The method of claim 19, wherein carriers generated by the single X-ray photon are determined to be collected by the first pixel and the second pixel, when the first voltage and the second voltage start to change in a same time period.

24. The method of claim 19, wherein carriers generated by the single X-ray photon are determined to be collected by the first pixel and the second pixel, when an absolute value of the first voltage and an absolute value of the second voltage reach a first threshold in a same time period.

25. The method of claim 19, wherein the X-ray photon is assigned to one of the first pixel and the second pixel to form an image, based on at least one of the following:
- a comparison of the first voltage and the second voltage; and
- relative positions of the two pixels.

26. A system suitable for phase-contrast X-ray imaging (PCI), the system comprising:
- the apparatus of claim 1;
- a second X-ray detector; and
- a spacer, wherein the apparatus and the second X-ray detector are spaced apart by the spacer.

27. The system of claim 26, wherein the apparatus and second X-ray detector are configured for respectively capturing an image of an object simultaneously.

28. The system of claim 26, wherein the second X-ray detector is identical to the apparatus.

* * * * *